United States Patent
Hyldig-Nielsen et al.

(10) Patent No.: US 7,108,980 B1
(45) Date of Patent: Sep. 19, 2006

(54) METHODS FOR THE ANALYSIS OF MICROCOLONIES OF BACTERIA AND YEAST

(75) Inventors: Jens J. Hyldig-Nielsen, Holliston, MA (US); Heather P. O'Keefe, Lexington, MA (US)

(73) Assignee: Boston Probes, Inc., Bedford, MA (US)

( * ) Notice: Subject to any disclaimer, the term of this patent is extended or adjusted under 35 U.S.C. 154(b) by 334 days.

(21) Appl. No.: 10/684,971

(22) Filed: Oct. 14, 2003

Related U.S. Application Data

(60) Division of application No. 09/822,763, filed on Mar. 30, 2001, now Pat. No. 6,656,687, which is a continuation of application No. 09/368,089, filed on Aug. 3, 1999, now Pat. No. 6,280,946.

(60) Provisional application No. 60/095,628, filed on Aug. 7, 1998.

(51) Int. Cl.
*C12Q 1/68* (2006.01)

(52) U.S. Cl. .......................................................... 435/6
(58) Field of Classification Search ..................... 435/6
See application file for complete search history.

(56) References Cited

U.S. PATENT DOCUMENTS

| | | | |
|---|---|---|---|
| 5,401,631 A | 3/1995 | Lane | |
| 5,434,048 A | 7/1995 | Simon et al. | 435/6 |
| 5,610,060 A | 3/1997 | Ward | |
| 5,654,418 A | 8/1997 | Sheiness | |
| 5,712,095 A | 1/1998 | Britschgi et al. | 435/6 |
| 5,747,277 A * | 5/1998 | Tsuchiya | 435/34 |
| 5,958,689 A | 9/1999 | Scholin et al. | 435/6 |
| 5,985,563 A | 11/1999 | Hyldig-Nielsen et al. | 435/6 |
| 6,664,045 B1 * | 12/2003 | Hyldig-Nielsen et al. | 435/6 |
| 6,750,039 B1 * | 6/2004 | Bargoot et al. | 435/34 |

FOREIGN PATENT DOCUMENTS

| | | |
|---|---|---|
| EP | 0692540 | 1/1996 |
| WO | WO88/03957 | 6/1988 |
| WO | WO89/02476 | 3/1989 |
| WO | WO89/06704 | 7/1989 |
| WO | WO90/01560 | 2/1990 |
| WO | WO90/15157 | 12/1990 |
| WO | WO96/22392 | 7/1996 |
| WO | WO 96/37177 | 11/1996 |

(Continued)

OTHER PUBLICATIONS

U.S. Appl. No. 09/225,048, filed Jan. 4, 1999, Gildea et al.

(Continued)

*Primary Examiner*—Kenneth R. Horlick
(74) *Attorney, Agent, or Firm*—Brian D. Gildea

(57) ABSTRACT

This invention is related to methods pertaining to the determination of bacteria and yeast wherein the methods comprise: a) filtering a sample containing bacteria and yeast through at least one filter; b) treating the filter or filters with a medium which facilitates the growth of the bacteria and yeast; c) growing the bacteria and yeast on the filter or filters to thereby produce colonies or microcolonies of the bacteria and yeast; d) fixing the colonies or microcolonies to the filter or filters; e) treating each filter under suitable hybridization conditions with one or more enzyme labeled PNA probes wherein, each PNA probe comprises a probing nucleobase sequence complementary to a target sequence in the nucleic acid of the bacteria and/or yeast; f) removing excess enzyme labeled PNA probe from each of the filters; and g) determining enzyme activity remaining on each filter to thereby identify or enumerate colonies or microcolonies on the filter or filters.

8 Claims, 8 Drawing Sheets

Culture Based Assay of Eucarya and Bacteria

FOREIGN PATENT DOCUMENTS

WO            WO88/03957           6/1998

OTHER PUBLICATIONS

U.S. Appl. No. 60/072,772, filed Jan. 27, 1998, Gildea et al.

Amann, R.I. et al, Combination of 16S rRNA-Targeted Oligonucleotide Probes with Flow Cytometry for Analyzing Mixed Microbial Populations. Appl. & Environ. Microbial. 56, 1919-1925 (1990).

Amann, R.I. et al, Phylogenetic Identification and In Situ Detection of Individual Microbial Cells without Cultivation. Microbio. Reviews 59, 143-169 (1995).

Chui, L. et al, Development of the Polymerase Chain Reaction for Diagnosis of Chancroid. J. Clin. Microbiol. 31, 659-664 (1993).

Giovannoni, S.J. et al, Phylogenetic Group-Specific Oligodeoxynucleotide Probes for Identification of Single Microbial Cells, J. of Bacteriol. 170, 720-726 (1988).

Hicks, R.E. et al, Dual Staining of Natural Bacterioplankton with 4',6-Diamidino-2-Phenylindole and Fluorescent Oligonucleotide Probes Targeting Kingdom-Level 16S rRNA Sequences. Appl. & Envir. Microbiol. 58, 2158-2163 (1992).

Jones, C.L. et al, An Oligonucleotide Probe to Assay Lysis and DNA Hybridization of a Diverse Set of Bacteria. Analy. Biochem. 181, 23-27 (1989).

McGregor, D.P. et al, Simultaneous Detection of Microorganisms in Soil Suspension Based on PCR Amplification of Bacterial 16S rRNA Fragments. Bi Tech. 21, 463-471 (1996).

Miller, P.E. et al, Identification of Cultured *Pseudo-nitzschia* (Bacillariophyceae) using Species-Specific LSU rRNA-targeted Fluorescent Probes, J. Phy 1. 32, 646-655 (1996).

Pluskal, M. et al, Peptide Nucleic Acid Probes and their Application in DNA and RNA Blot Hybridization Analysis. American Society for Biochemistry and Molecular Biology. Abstract #35. 85th Annual Meeting, Washington, DC May 21-25, 1994.

Rice, J. et al, Fluorescent oligonucleotide rDNA probes that specifically bind to a common nanoflagellate, *Paraphysomonas vestita.* Microbi 1. 143, 1717-1727 (1997).

Rooney-Varga, J.N. et al, Seasonal Changes in the Relative Abundance of Uncultivated Sulfate-Reducing Bacteria in a Salt Marsh Sediment and in the Rhizosphere of *Spartina alterniflora.* Appl. & Envir n. Micr bi l. 63, 3895-3901 (1997).

Seal, S.E. et al, Differentiation of *Pseudomonas solanacearum, Pseudomonas syzygii, Pseudomonas pickettii* and the Blood Disease Bacterium by partial 16S rRNA sequencing: construction of oligonucleotide primers for sensitive detection by polymerase chain reaction. J. Gen. Microbiol. 139, 1587-1594.

Stefano, K. et al, Diagnostic Applications of PNA Oligomers. Diagnostic Gene Detection and Quantification Technologies for Infectious Agents and Human Genetic Diseases. #948 IBC Library Series, 19-37 (1997).

Von Wintzingerode, F. et al, Identification of environmental strains of *Bacillus mycoides* by fatty acid analysis and species-specific 16S rDNA oligonucleotide probe. FEMS Microbiol. Ecol. 24, 201-209 (1997).

Zarda, B. et al, Analysis of bacterial community structure in bulk soil by in situ hybridization. Arch. Microbiol. 168, 185-192 (1997).

* cited by examiner

Figure 5 EuUni-1 vs BacUni-1

Figure 6
Multiplex Detection
I
Visualization of Saccharomyces with Rho-EuUni-1
II
Visualization of E. coli with Flu-BacUni-1
III
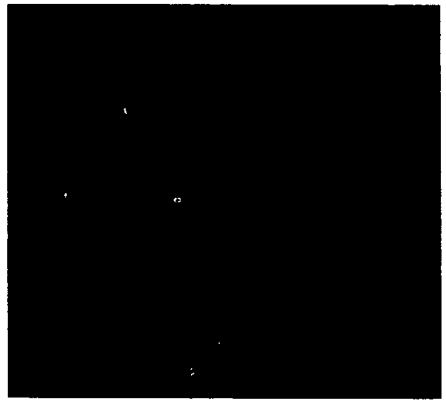
Visualization of both labels with a triple filter in the microscope and a FITC filter in the camera
IV
Computer generated composite images ( I and II ).

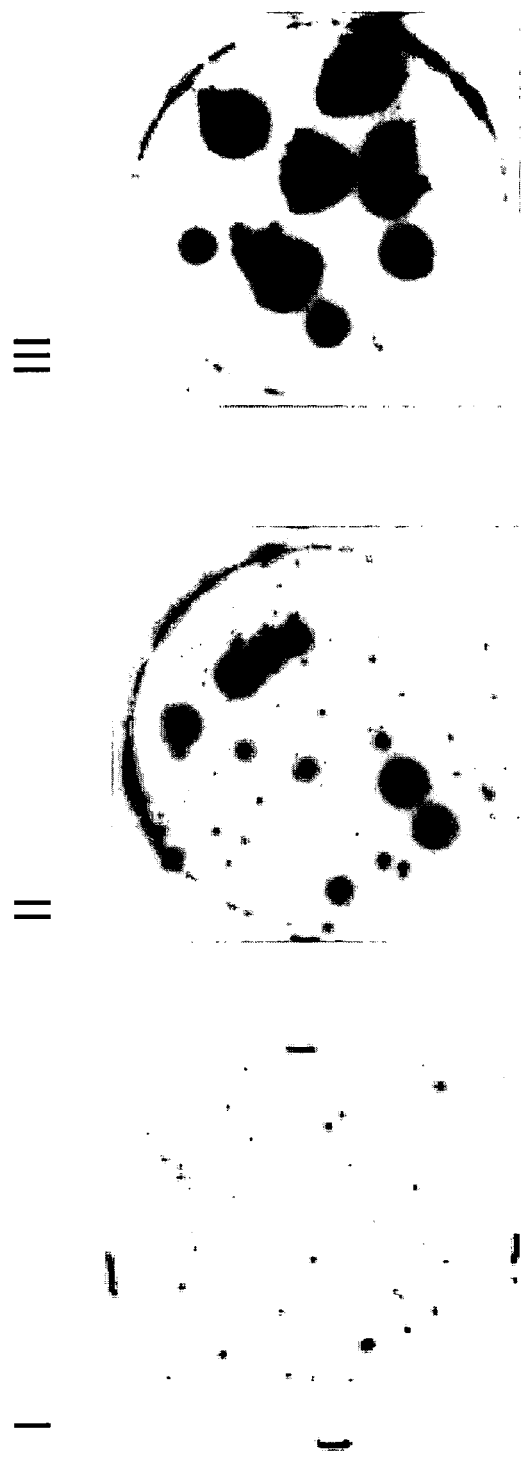
Figure 8  Culture Based Assay of Eucarya and Bacteria

SEQUENCE LISTING

```
<160> NUMBER OF SEQ ID NOS: 8

<210> SEQ ID NO 1
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 1
ctgcctcccg tagga                                                     15

<210> SEQ ID NO 2
<211> LENGTH: 16
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 2
taccagggta tctaat                                                    16

<210> SEQ ID NO 3
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 3
cacgagctga cgaca                                                     15
```

```
<210> SEQ ID NO 4
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 4
ccgacaagga atttc                                                      15

<210> SEQ ID NO 5
<211> LENGTH: 16
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 5
accagacttg ccctcc                                                     16

<210> SEQ ID NO 6
<211> LENGTH: 16
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 6
gggcatcaca gacctg                                                     16

<210> SEQ ID NO 7
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence

<400> SEQUENCE: 7
tagaaagggc aggga                                                      15

<210> SEQ ID NO 8
<211> LENGTH: 15
<212> TYPE: DNA
<213> ORGANISM: Artificial Sequence
<220> FEATURE:
<223> OTHER INFORMATION: Description of Combined DNA/RNA Molecule:
      Probing Nucleobase Sequence
<220> FEATURE:
<223> OTHER INFORMATION: Description of Artificial Sequence:Probing
      Nucleobase Sequence
```

```
-continued

<400> SEQUENCE: 8
tacaaagggc aggga                                          15
```

METHODS FOR THE ANALYSIS OF MICROCOLONIES OF BACTERIA AND YEAST

CROSS REFERENCE TO RELATED APPLICATIONS

The application is a division of U.S. Ser. No. 09/822,763 filed on Mar. 30, 2001 (now U.S. Pat. No. 6,656,687) which is a continuation of U.S. Ser. No. 09/368,089 filed on Aug. 3, 1999 (now U.S. Pat. No. 6,280,946) which application claims the benefit of U.S. Provisional Patent Application Ser. No. 60/095,628 filed on Aug. 7, 1998, all of which are incorporated herein by reference.

BACKGROUND OF THE INVENTION

1. Field of the Invention

This invention is related to the field of probe-based detection, analysis and quantitation of bacteria and eucarya. More specifically, this invention relates to novel PNA probes, probe sets, methods and kits which can be used to detect, identify or quantitate one or more bacteria and/or eucarya which may be present in a sample.

2. Description of the Related Art

Nucleic acid hybridization is a fundamental process in molecular biology. Probe-based assays are useful in the detection, quantitation and analysis of nucleic acids. Nucleic acid probes have long been used to analyze samples for the presence of nucleic acid from bacteria, fungi, virus or other organisms and are also useful in examining genetically-based disease states or clinical conditions of interest. Nonetheless, probe-based assays have been slow to achieve commercial success. This lack of commercial success is, at least partially, the result of difficulties associated with specificity, sensitivity and reliability.

Hybridization assays hold promise as a means to screen large numbers of samples for conditions of interest. In practice, however, it is often difficult to multiplex a hybridization assay given the requirement that each of the many very different probes in the assay must exhibit a very high degree of specificity for a specific target nucleic acid under the same or similar conditions of stringency. Given the difficulties in specificity, sensitivity and reliability of nucleic acid probes in assays designed to detect a single target nucleic acid, sensitive and reliable methods for the multiplex analysis of samples have been particularly elusive.

The in-situ targeting of rRNA as a means to detect, identify or quantitate organisms is well established (See: Amann et al., *Microbiological Reviews*, 59: 143–169 (1995). Nucleic acid probes for the universal detection of bacteria and eucarya having the same or similar nucleobase composition to the PNA probes claimed herein can be found in Table 3 of Amann et al. The table lists probes and nucleic acid sequences derived from relevant scientific literature.

Despite its name, Peptide Nucleic Acid (PNA) is neither a peptide, a nucleic acid nor is it an acid. Peptide Nucleic Acid (PNA) is a non-naturally occurring polyamide which can hybridize to nucleic acid (DNA and RNA) with sequence specificity (See: U.S. Pat. No. 5,539,082 and Egholm et al., *Nature* 365: 566–568 (1993)). Being a non-naturally occurring molecule, unmodified PNA is not known to be a substrate for the enzymes which are known to degrade peptides or nucleic acids. Therefore, PNA should be stable in biological samples, as well as have a long shelf-life. Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.* 118:5544–5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay, appears to be somewhat sequence dependent (Nielsen et al., *Anti-Cancer Drug Design* 8:53–65, (1993) and Weiler et al., *Nucl. Acids Res.* 25: 2792–2799 (1997)).

Though they hybridize to nucleic acid with sequence specificity (See: Egholm et al., *Nature*, at p. 567), PNAs have been slow to achieve commercial success at least partially due to cost, sequence specific properties/problems associated with solubility and self-aggregation (See: Bergman, F., Bannwarth, W. and Tam, S., *Tett. Lett.* 36:6823–6826 (1995), Haaima, G., Lohse, A., Buchardt, O. and Nielsen, P. E., *Angew. Chem. Int. Ed. Engl.* 35:1939–1942 (1996) and Lesnik, E., Hassman, F., Barbeau, J., Teng, K. and Weiler, K., *Nucleosides &Nucleotides* 16:1775–1779 (1997) at p 433, col. 1, ln. 28 through col. 2, ln. 3) as well as the uncertainty pertaining to non-specific interactions which might occur in complex systems such as a cell (See: Good, L. et al., *Antisense & Nucleic Acid Drug Development* 7:431–437 (1997)). Consequently, their unique properties clearly demonstrate that PNA is not the equivalent of a nucleic acid in either structure or function. Thus, PNA probes need to be evaluated for performance and optimization to thereby confirm whether they can be used to specifically and reliably detect a particular nucleic acid target sequence, particularly when the target sequence exists in a complex sample such as a cell, tissue or organism.

PNA probes have been demonstrated as being useful for the detection of rRNA in ISH and FISH assays (See: WO95/32305 and WO97/18325). PNA probes have also been used in the analysis of mRNA (e.g. Kappa Light Chain), viral nucleic acid (e.g. human papillomavirus) and the analysis of centromeric sequences in human chromosomes and human telomeres (See: Lansdorp et al., *Human Mol. Genetics*, 5: 685–691 (1996) as well as WO97/14026). Similarly, the analysis of trinucleotide repeats in chromosomal DNA using appropriate PNA probes has been suggested (See: WO97/14026). A PNA probe has also been used to detect human X chromosome specific sequences in a PNA-FISH format (See: WO97/18325).

Any method, kits or compositions which could improve the specificity, sensitivity and reliability of probe-based assays for the detection of microorganisms in samples of interest would be a useful advance in the state of the art particularly where the methods were uniformly applicable to probes of all or substantially all sequence variations. Moreover, the methods, kits or compositions would be particularly useful if they could provide for the rapid, reliable and sensitive multiplex analysis of samples for the presence or absence of microorganisms and particularly bacteria and/or eucarya. The probes and assays would be particularly useful if they were well suited for the detecting, identifying or quantitating only colony forming units (viable organisms) in a sample.

SUMMARY OF THE INVENTION

This invention is directed to PNA probes, probe sets, methods and kits useful for the universal detection, identification and/or enumeration of bacteria and/or eucarya in a sample. The preferred probing nucleobase sequence of the universal probes of this invention are listed in Table 1, below. In preferred embodiments, PNA probes are organized into a set which is designed to detect, identify or quantitate the bacteria and/or eucarya which may be present in the sample. In a most preferred embodiment, the probe set is suitable for the specific detection, identification and/or quantitation of the total bacteria and/or total eucarya present in a sample.

Unique PNA probe constructs of this invention also include probes comprising two or more different types of labels such as the use of a hapten/fluorophore (e.g. fluorescein) in combination with an enzyme (e.g. soy bean peroxidase). Such orthogonally labeled probes can be experimental controls used in complex analysis systems or otherwise merely be used to provide alternative detection methodologies.

This invention is further directed to a method suitable for detecting, identifying or quantitating one or more bacteria and/or one or more eucarya in a sample. The method comprises contacting the sample with one or more PNA probes, wherein suitable probes are described herein. According to the method, bacteria and/or eucarya are then detected, identified or quantitated. Detection, identification and/or quantitation is made possible by correlating the hybridization, under suitable hybridization conditions, of the probing nucleobase sequence of a PNA probe to the target sequence of bacteria or eucarya in the sample to thereby determine the presence, absence or number of bacteria and/or eucarya in the sample. This correlation is made possible by direct or indirect detection of the probe/target sequence hybrid.

In yet another embodiment, this invention is also directed to kits suitable for performing an assay which detects, identifies or quantitates the bacteria and/or eucarya in a sample. The kits of this invention comprise one or more PNA probes (as described herein) and other reagents or compositions which are selected to perform an assay or otherwise simplify the performance of an assay.

The PNA probes, probe sets, methods and kits of this invention have been demonstrated to be specific and yet universal for either bacteria or eucarya by the Examples contained herein. By "specific and yet universal" we mean that the PNA probes of this invention, either alone or in combination, detect target sequences within virtually all bacteria or eucarya, as the case may be, without any substantial cross reaction with non-target organisms. By "virtually all bacteria or eucarya" we mean that less than 2–4 percent of the target organisms will not be detectable with these universal probes (based on analysis of sequence information available in Genebank 104). By "without substantial cross reaction" we mean that less than 2–4 percent of non-target organisms will be detected when using these probes (based on analysis of sequence information available in Genebank 104). Moreover, the assays described herein are rapid (the entire assay can typically be performed in 3 hours or less with the probe hybridization requiring only 15–60 minutes), sensitive, reliable and generally applicable to probes of significantly different probing nucleobase sequence length and sequence variation. They can be used in an assay to accurately detect, identify and/or quantitate the total bacteria and/or total eucarya in a sample.

This invention is also directed to a multiplex PNA in-situ hybridization (PNA-ISH) assay and particularly a PNA-FISH assay. As a demonstration of the versatility of the PNA probes, probe sets, methods and kits of this invention, a fluorescent in-situ hybridization assay was multiplexed without any change to the protocol. The assay clearly provided for the detection, classification and/or enumeration of bacteria and eucarya in the sample (See: Example 12, herein). Thus, Applicants have demonstrated (believed to be the first successful example) the feasibility of a multiplex PNA-FISH assay which is suitable for, in a single assay, positively detecting, characterizing and quantitating the total bacteria and/or total eucarya present in a sample.

Since probe-based analysis detects nucleic acid without regard to the metabolic state of the organism in which the genetic material exists, the analysis of cells in culture is preferably used to distinguish between viable organisms and dead (non-viable) organisms, the presence of which are generally not considered to cause spoilage or contamination. Consequently, this invention is further directed to a rapid culture-based detection, identification and/or enumeration of total viable bacteria and/or total viable eucarya in a sample of interest.

The PNA probes, probe sets, methods and kits of this invention are particularly useful for the detection, identification and/or enumeration of bacteria and eucarya (e.g. pathogens) in food, beverages, water, pharmaceutical products, personal care products, dairy products or environmental samples. The analysis of preferred non-limiting beverages include soda, bottled water, fruit juice, beer, wine or liquor products. Suitable PNA probes, probe sets, methods and kits will be particularly useful for the analysis of raw materials, equipment, products or processes used to manufacture or store food, beverages, water, pharmaceutical products, personal care products dairy products or environmental samples.

Additionally, the PNA probes, probe sets, methods and kits of this invention are particularly useful for the detection of bacteria and eucarya (e.g. pathogens) in clinical samples and clinical environments. Suitable PNA probes, probe sets, methods and kits will be particularly useful for the analysis of clinical specimens, equipment, fixtures or products used to treat humans or animals.

BRIEF DESCRIPTION OF THE DRAWINGS

FIGS. 6-I through 6-IV are individual or composite digital images of the same section of a sample slide containing bacteria and eucarya which were treated with two universal PNA probes wherein the PNA probes are independently detectable for either bacteria (green fluorescence) and eucarya (red fluorescence). The images were obtained using a fluorescence microscope and commercially available light filters fitted to the microscope and the camera respectively. Panel 6-I is the image obtained using a red microscope filter and red camera filter; Panel 6-II is the image obtained using a green microscope filter and green camera filter; Panel 6-III is the image obtained using a triple (green, red and blue) microscope filter (wherein the camera image records on the image obtained with the green camera filter); and Panel 6-IV is a digitally created composite of the images presented in Panels 6-I and 6-II.

FIGS. 8I–III are electronic images of X-ray film analysis of colonies of yeast and bacteria grown from organisms isolated from a liquid sample using a round membrane filter wherein the colonies are detected using in-situ hybridization with the SBP-labeled PNA probes, specific yet universal for either bacteria or eucarya, directly on the membrane filter from which the organisms were isolated and colonies grown.

DETAILED DESCRIPTION OF THE INVENTION

Figure 1:
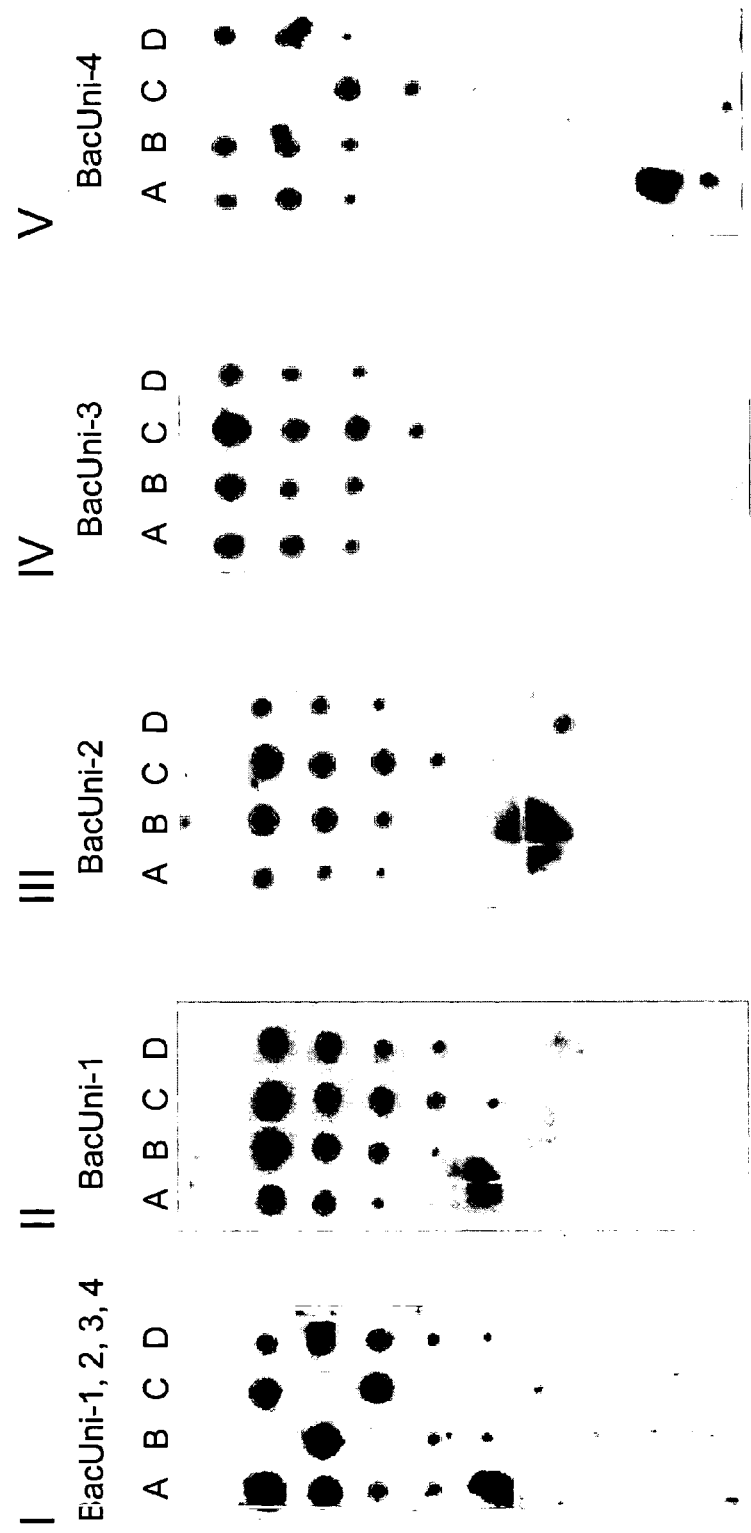
FIGS. 1-I through 1-V are electronic images of dot blot assays used to examine the individual (Panels II–V) and combined (Panel I) universal detectability of 4 different fluorescein labeled (fluorescein used as a hapten in the experiment) PNA oligomers directed to target sequences in the rRNA of bacteria.

1. Definitions a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

b. As used herein, the term "nucleobase sequence" is any segment of a polymer which comprises nucleobase containing subunits. Non-limiting examples of suitable polymers or polymers segments include oligonucleotides, oligoribonucleotides, peptide nucleic acids, nucleic acid analogs, nucleic acid mimics or chimeras.

c. As used herein, the term "target sequence" is the nucleic acid nucleobase sequence of bacteria and/or eucarya which is to be detected in an assay and to which at least a portion of the probing nucleobase sequence is designed to hybridize.

d. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diederichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 11:5 55–560 (1997); Petersen et al., *Bioorg. Med. Chem. Lett.* 6: 793–796 (1996); Diederichsen, U., *Bioorganic &Med. Chem. Lett.,* 8: 165–168 (1998); Cantin et al., *Tett. Lett.,* 38: 4211–4214 (1997); Ciapetti et al., *Tetrahedron,* 53: 1167–1176 (1997); Lagriffoule et al., *Chem. Eur. J.,* 3: 912–919 (1997) and WIPO patent application WO96/04000 by Shah et al. and entitled "Peptide-based nucleic acid mimics (PENAMs)".

In preferred embodiments, a PNA is a polymer comprising two or more subunits of the formula:

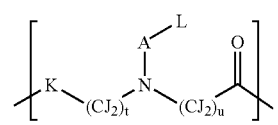

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$— and a group of the formula; —$(CJ_2)_sC(O)$—, wherein, J is defined above and each s is an whole number from one to five. The whole number t is 1 or 2 and the whole number u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

e. As used herein, the terms "label" and "detectable moiety" shall be interchangeable and shall refer to moieties which can be attached to a PNA probe, antibody or antibody fragment to thereby render the probe, antibody or antibody fragment detectable by an instrument or method.

f. As used herein, the term "chimera" or "chimeric oligomer" shall mean an oligomer comprising two or more linked subunits which are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

g. As used herein, the term "linked polymer" shall mean a polymer comprising two or more polymer segments which are linked by a linker. The polymer segments which are linked to form the linked polymer are selected from the group consisting of an oligodeoxynucleotide, an oligoribonucleotide, a peptide, a polyamide, a peptide nucleic acid (PNA) and a chimera.

2. Description

I. General

PNA Synthesis

Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of peptide nucleic acids are now commercially available. Both labeled and unlabeled PNA oligomers are likewise available from commercial vendors of custom PNA oligomers. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling

Preferred non-limiting methods for labeling non-nucleic acid probes and PNAs are described in WO98/24933, WO99/22018, WO99/21881, WO99/37670; copending and co-owned applications U.S. Ser. No. 09/179,298, U.S. Ser. No. 09/179,162, U.S. Ser. No. 09/225,048 and U.S. Ser. No. 09/275,848 (herein incorporated by reference), the priority documents listed as related applications, the examples section of this specification or are otherwise well known in the art of PNA synthesis (See: Nielsen, P. E., Egholm, M., *Peptide Nucleic Acids*, Horizon Scientific Press (1999) pp. 81–86).

Labels

Non-limiting examples of detectable moieties (labels) suitable for labeling PNA probes or antibodies used in the practice of this invention would include a dextran conjugate, a branched nucleic acid detection system, a chromophore, a fluorophore, a spin label, a radioisotope, an enzyme, a hapten, an acridinium ester and a chemiluminescent compound. Other suitable labeling reagents and preferred methods of attachment would be recognized by those of ordinary skill in the art of PNA, peptide or nucleic acid synthesis.

Preferred haptens include 5(6)-carboxyfluorescein, 2,4-dinitrophenyl, digoxigenin, and biotin.

Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine dyes 2, 3, 3.5, 5 and 5.5 are available as NHS esters from Amersham, Arlington Heights, Ill.) or the Alexa dye series (Molecular Probes, Eugene, Oreg.).

Preferred enzymes include polymerases (e.g. Taq polymerase, Klenow DNA polymerase, T7 DNA polymerase, Sequenase, DNA polymerase 1 and phi29 polymerase), alkaline phosphatase (AP), horseradish peroxidase (HRP) and most preferably, soy bean peroxidase (SBP).

Detectable and Independently Detectable Moieties/Multiplex Analysis

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, one or more distinct independently detectable moieties are used to label two or more different probes used in an assay. The ability to differentiate between and/or quantitate each of the independently detectable moieties provides the means to multiplex a hybridization assay because the data which correlates with the hybridization of each of the distinctly (independently) labeled probe to a particular target sequence can be correlated with the presence, absence or quantity of each organism sought to be detected in the sample. Consequently, the multiplex assays of this invention may be used to simultaneously detect the presence, absence or quantity of two or more organisms in the same sample and in the same assay.

Spacer/Linker Moieties

Generally, spacers are used to minimize the adverse effects that bulky labeling reagents might have on hybridization properties of probes. Linkers typically induce flexibility and randomness into the probe or otherwise link two or more nucleobase sequences of a probe or component polymer. Preferred spacer/linker moieties for the nucleobase polymers of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255–7258 (1998)). Preferably, a spacer/linker moiety comprises one or more linked compounds having the formula: $-Y-(O_m-(CW_2)_n)_o-Z-$. The group Y is selected from the group consisting of: a single bond, $-(CW_2)_p-$, $-C(O)(CW_2)_p-$, $-C(S)(CW_2)_p-$ and $-S(O_2)(CW_2)_p$. The group Z has the formula NH, $NR^2$, S or O. Each W is independently H, $R^2$, $-OR^2$, F, Cl, Br or I; wherein, each $R^2$ is independently selected from the group consisting of: $-CX_3$, $-CX_2CX_3$, $-CX_2CX_2CX_3$, $-CX_2CX(CX_3)_2$, and $-C(CX_3)_3$. Each X is independently H, F, Cl, Br or I. Each m is independently 0 or 1. Each n, o and p are independently integers from 0 to 10.

Hybridization Conditions/Stringency

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of a PNA to a nucleic acid, except that the hybridization of a PNA is fairly independent of ionic strength. Optimal stringency for an assay may be experimentally determined by examination of each stringency factor until the desired degree of discrimination is achieved.

Suitable Hybridization Conditions

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods and compositions described herein. Suitable in-situ hybridization conditions are those conditions suitable for performing an in-situ hybridization procedure. Thus, suitable in-situ hybridization conditions will become apparent using the disclosure and references herein; with or without additional routine experimentation.

Blocking Probes

Blocking probes are nucleic acid or non-nucleic acid probes which can be used to suppress the binding of the probing nucleobase sequence of the probing polymer to a non-target sequence. Preferred blocking probes are PNA probes (See: Coull et al., WIPO publication No. WO98/24933). Typically blocking probes are closely related to the probing nucleobase sequence and preferably they comprise a point mutation of the probing segment. It is believed that blocking probes operate by hybridization to the non-target sequence to thereby form a more thermodynamically stable complex than is formed by hybridization between the probing nucleobase sequence and the non-target sequence. Formation of the more stable and preferred complex blocks formation of the less stable non-preferred complex between the probing nucleobase sequence and the non-target sequence. Thus, blocking probes can be used with the methods, kits and compositions of this invention to suppress the binding of the nucleic acid or non-nucleic acid probe to a non-target sequence which might be present and interfere with the performance of the assay. Blocking probes are particularly advantageous in single point mutation discrimination.

Probing Nucleobase Sequence

The probing nucleobase sequence of a PNA probe is the specific sequence recognition portion of the construct. Therefore, the probing nucleobase sequence is a sequence of PNA subunits designed to hybridize to a target sequence to thereby be used to detect the presence, absence or number of organisms of interest in a sample. Consequently, with due consideration of the requirements of a PNA probe for the assay format chosen and the organism sought to be detected, the length of the probing nucleobase sequence of the PNA probe will generally be chosen such that a stable complex is formed with the target sequence under suitable hybridization conditions or suitable in-situ hybridization conditions.

The probing nucleobase sequence suitable for detecting the target organism listed in the table, will generally, but not necessarily, have a length of 16 or fewer PNA subunits (most preferably 7–16 subunits in length) wherein at least a portion of the probing nucleobase sequence is at least ninety percent homologous to the nucleobase sequences listed in Table 1, or their complements. Longer probing nucleobase sequences may be used but they are not preferred. Complements of the probing nucleobase sequence are included since it is possible to prepare or amplify copies of the target sequence wherein the copies are complements of the target sequence and thus, will bind to the complement of the probing nucleobase sequences listed in Table 1. The most preferred probing nucleobase sequences are listed in Table 1. These probing nucleobase sequences have been shown to be specific yet universal for the target organism identified in the table.

The probing nucleobase sequence of a PNA probe will generally be complementary to the target sequence. Alternatively, a substantially complementary probing nucleobase sequence might be used since it has been demonstrated that greater sequence discrimination can be obtained when utilizing probes wherein there exists one or more point mutations (base mismatch) between the probe and the target sequence (See: Guo et al., *Nature Biotechnology* 15:331–335 (1997)). For example, probing nucleobase sequences 7 and 8 of Table 1 differ by a single nucleobase (e.g. a point mutation). It is also noteworthy that probing nucleobase sequences 7 and 8 are particularly purine rich and the literature teaches that such PNA sequences are difficult or impossible to purify and characterize (See: Nielsen, P. E., Egholm, M., *Peptide Nucleic Acids*, Horizon Scientific Press (1999) p 253). Table 3 of Amann et al. identifies a nucleic acid probe having a nucleobase sequence identical to the probing nucleobase sequence listed as Sequence ID No. 7 (See: Amann et al., *Microbiological Reviews*, 59: 143–169 (1995). Examination of Genbank 104 indicates that Sequence ID No. 8 is perfectly homologous to the rRNA of substantially all eucarya for which information exists in the databank. The sequences are related as point mutations having a 93.3 percent sequence homology. The Examples and Figures of this specification indicate that the both probing nucleobase sequences 7 and 8 of Table 1 are suitable for the specific yet universal detection of eucarya. Thus, the data presented herein supports the premise that PNA probes having a sequence homology of ninety percent or greater are useful equivalents of the exact probing nucleobase sequences identified in Table 1.

This invention contemplates that variations in the probing nucleobase sequences listed in Table 1 shall provide PNA probes which are suitable for the specific detection of the organisms listed. Common variations include, deletions, insertions and frame shifts. Variation of the probing nucleobase sequences within the parameters described herein are considered to be an embodiment of this invention.

Probe Complexes

In still another embodiment, two probes are designed to hybridize to the target sequence sought to be detected to thereby generate a detectable signal whereby the probing nucleobase sequence of each probe comprises the complement to half or approximately half of the complete target sequence of the bacteria or eucarya sought to be detected in the assay. As a non-limiting example, the probing nucleobase sequences of the two probes might be designed using the assay as described in European Patent Application 849,363, entitled "Method of identifying a nucleic acid using triple helix formation of adjacently annealed probes" by H. Orum et al. (See: EPA 849,363). Using this methodology, the probes which hybridize to the target sequence may or may not be labeled. However, it is the probe complex formed by the annealing of the adjacent probes which is detected. Similar compositions comprised solely of PNA probes have been described in copending and commonly owned application U.S. Ser. No. 09/302,238, herein incorporated by reference.

II. Preferred Embodiments of the Invention a. PNA Probes

In one embodiment, this invention is directed to PNA probes. The PNA probes of this invention are, alone or in combination, suitable for detecting, identifying or quantitating bacteria and/or eucarya in a sample. General characteristics (e.g. length, labels, nucleobase sequences, linkers etc.) of PNA probes suitable for the detection, identification or quantitation of bacteria and/or eucarya have been previously described herein. The preferred probing nucleobase sequences of PNA probes of this invention are listed in Table 1.

TABLE 1

| Sequence ID No. | Probe Type | Target Organism | rRNA Target | Probing Nucleobase Sequence |
|---|---|---|---|---|
| 1 | Universal | Bacteria | 16S | CTG-CCT-CCC-GTA-GGA |
| 2 | Universal | Bacteria | 16S | TAC-CAG-GGT-ATC-TAA-T |
| 3 | Universal | Bacteria | 16S | CAC-GAG-CTG-ACG-ACA |
| 4 | Universal | Bacteria | 23S | CCG-ACA-AGG-AAT-TTC |
| 5 | Universal | Eucarya | 18S | ACC-AGA-CTT-GCC-CTC-C |
| 6 | Universal | Eucarya | 18S | GGG-CAT-CAC-AGA-CCT-G |
| 7 | Universal | Eucarya | 18S | TAG-AAA-GGG-CAG-GGA |
| 8 | Universal | Eucarya | 18S | TAC-AAA-GGG-CAG-GGA |

Note: Apart from the functional Examples described herein which have been performed to screen potential probe sequences and thereby confirm their practical specificity in an assay, the complementary target sequence to which the probing nucleobase sequences in Table 1 hybridize were examined using sequence alignment analysis of information currently available in Genbank.

The PNA probes of this invention may comprise only a probing nucleobase sequence (as previously described herein) or may comprise additional moieties. Non-limiting examples of additional moieties include detectable moieties (labels), linkers, spacers, natural or non-natural amino acids, or other subunits of PNA, DNA or RNA. Additional moieties may be functional or non-functional in an assay. Generally however, additional moieties will be selected to be functional within the design of the assay in which the PNA probe is to be used. The preferred PNA probes of this invention are labeled with one or more detectable moieties. In a more preferred embodiment, one or more probes are labeled with a set of two or more independently detectable moieties. Preferred sets of independently detectable moieties are comprised of independently detectable labels each individually selected from the group consisting of fluorophores, enzymes and haptens.

Unique PNA probe constructs of this invention also include probes comprising two or more different types of labels (orthogonal labels) such as the use of a hapten/fluorophore (e.g. fluorescein) in combination with an enzyme (e.g. soy bean peroxidase). Such orthogonally labeled probes can be experimental controls used to analyze complex analysis systems or otherwise merely be used to provide alternative detection methodologies. By orthogonally labeled probes we mean that the two labels are of such different character that a completely different type of detection system can be used to detect the orthogonal labels. For example, two independently detectable fluorophores are not necessarily orthogonal labels since fluorescence detection is common to the detection system. However, fluorescence used in combination with an enzyme is orthogonal since detection of the two labels can require completely different detection methodologies.

It is an important feature of this invention that PNA probes of this invention can be used to target both bacteria and eucarya in the same assay under the same set of conditions. This is surprising since the cell walls of yeast are substantially different as compared with bacteria. Consequently, typical conditions for in-situ analysis of yeast and bacteria using nucleic acid probes are often substantially different. In a most preferred embodiment of this invention, independently detectable moieties are used to label each of at least two different PNA probes whereby at least one probe is a universal probe for detecting bacteria and at least one other probe is a universal probe for detecting eucarya such that the independently detectable moieties can be used to independently detect, identify or quantitate the bacteria and/or the eucarya in the same sample and in the same assay. Examples 12 and 13 of this specification demonstrates the feasibility of multiplex PNA-FISH and PNA-ISH, respectively, for the simultaneous analysis of yeasts and bacteria present in the same sample.

In preferred embodiments, the probes of this invention are used in in-situ hybridization (ISH) and fluorescence in-situ hybridization (FISH) assays. Excess probe used in a ISH or FISH assay typically must be removed so that the detectable moiety of specifically bound probes can be detected above the background signal which results from still present but unhybridized probe. Generally, the excess probe is washed away after the sample has been incubated with probe for a period of time. However, use of dark probes are a preferred embodiment of this invention, since there is no requirement that excess dark probe be completely removed (washed away) from the sample since it generates little or no detectable background.

As used herein, a "dark probe" shall be a PNA probe which hybridizes to a nucleic acid target to thereby cause a detectable change in at least one physical property of at least one attached label in a manner which can be used to detect, identify or quantitate the presence of an organism of interest in a sample of interest. Non-limiting examples of dark probes include PNA Molecular Beacons (See: WO99/21881, U.S. Ser. No. 08/958,532 (abandoned) and copending and commonly owned U.S. Ser. No. 09/179,298, both incorporated herein by reference) as well as Linear Beacons (See: WO99/22018 and copending and commonly owned U.S. Ser. No. 09/179,162, herein incorporated by reference). Thus, changes in signal in the assay utilizing a "dark probe" can be directly correlated with hybridization of the probing nucleobase sequence to the target sequence of bacteria or eucarya of interest.

Unlabeled Non-Nucleic Acid Probes

The probes of this invention need not be labeled with a detectable moiety to be operable within this invention. When using the probes of this invention it is possible to detect the probe/target sequence complex formed by hybridization of the probing nucleobase sequence of the probe to the target sequence. For example, a PNA/nucleic acid complex formed by the hybridization of a PNA probing nucleobase sequence to the target sequence could be detected using an antibody which specifically interacts with the complex under antibody binding conditions. Suitable antibodies to PNA/nucleic acid complexes as well as methods for their preparation and use are described in WIPO Patent Application WO95/17430 and U.S. Pat. No. 5,612,458, herein incorporated by reference.

The antibody/PNA/nucleic acid complex formed by interaction of the α-PNA/nucleic acid antibody with the PNA/nucleic acid complex can be detected by several methods. For example, the α-PNA/nucleic acid antibody could be labeled with a detectable moiety. Suitable detectable moieties have been previously described herein. Thus, the presence, absence or quantity of the detectable moiety is correlated with the presence, absence or quantity of the antibody/PNA/nucleic acid complex and the organism to be identified by the probing nucleobase sequence of the PNA probe. Alternatively, the antibody/PNA/nucleic acid complex is detected using a secondary antibody which is labeled with a detectable moiety. Typically the secondary antibody specifically binds to the α-PNA/nucleic acid antibody under antibody binding conditions. Thus, the presence, absence or quantity of the detectable moiety is correlated with the presence, absence or quantity of the antibody/antibody/PNA/nucleic acid complex and the organism to be identified by the probing nucleobase sequence of the probe. As used herein, the term antibody shall include antibody fragments which specifically bind to other antibodies or other antibody fragments.

Immobilization of Probes to a Surface

One or more of the PNA probes of this invention may optionally be immobilized to a surface for the detection of the target sequence of bacteria and/or eucarya. Generally, surface immobilized PNA probes can be used in a capture assay. PNA probes can be immobilized to the surface using the well known process of UV-crosslinking. More preferably, the PNA probe is synthesized on the surface in a manner suitable for deprotection but not cleavage from the synthesis support (See: Weiler, J. et al, Hybridization based DNA screening on peptide nucleic acid (PNA) oligomer arrays., Nucl. Acids Res., 25:2792–2799 (July, 1997)). In still another embodiment, one or more PNA probes are covalently linked to a surface by the reaction of a suitable functional group on the probe with a functional group of the surface (See: Lester, A. et al, "PNA Array Technology": Presented at Biochip Technologies Conference in Annapolis (October, 1997)). This method is most preferred since the PNA probes on the surface will typically be highly purified and attached using a defined chemistry, thereby minimizing or eliminating non-specific interactions.

Methods for the chemical attachment of probes to surfaces generally involve the reaction of a nucleophilic group, (e.g. an amine or thiol) of the probe to be immobilized, with an electrophilic group on the support to be modified. Alternatively, the nucleophile can be present on the support and the electrophile (e.g. activated carboxylic acid) present on the probe. Because native PNA possesses an amino terminus, a PNA will not necessarily require modification to thereby immobilize it to a surface (See: Lester et al., Poster entitled "PNA Array Technology").

Conditions suitable for the immobilization of a PNA probe to a surface will generally be similar to those conditions suitable for the labeling of the polymer. The immobilization reaction is essentially the equivalent of labeling whereby the label is substituted with the surface to which the polymer is to be linked.

Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

Arrays of PNA Probes or Probe Sets

Arrays are surfaces to which two or more probes have been immobilized each at a specified position. Typically, the probing nucleobase sequence of the immobilized probes is judiciously chosen to interrogate (often using a capture assay) a sample which may contain bacteria and/or eucarya. Because the location and composition of each immobilized probe is known, arrays are generally useful for the simultaneously detection, identification or quantitation of two or more organisms which may be present in the sample. Moreover, arrays of PNA probes may be regenerated by stripping the hybridized nucleic acid after each assay, thereby providing a means to repetitively analyze numerous samples using the same array. Thus, arrays of PNA probes or PNA probe sets may be useful for repetitive screening of samples for bacteria and/or eucarya. The arrays of this invention comprise at least one PNA probe (as described herein) suitable for the detection, identification or quantitation of bacteria and/or eucarya. Preferred probing nucleobase sequences for the immobilized PNA probes are listed in Table 1.

Advantages of Using PNA Probes

It has been demonstrated that nucleic acid probes hybridize to target sequences of rRNA (e.g. targets like 16S or 23S rRNA) with an efficiency which is highly dependent upon whether the site of hybridization is placed inside or outside of a highly structured region (See: Fuchs et al., Applied and Environmental Microbiology, 64: 4973–4982 (1998)). Moving the probe just a few bases in or out of a structured region significantly alters the overall signal intensity. The lack of signal intensity achieved when attempting to target structured rRNA is believed to result from the lack of probe accessibility to the hybridization site under suitable hybridization conditions or suitable in-situ hybridization conditions. Furthermore, conditions which would destabilize the structured region would simultaneously destabilize the target sequence/probe hybrid.

When designing nucleic acid probes directed to a target sequence which are to be used to select a target organism, nucleobase sequence selection is further limited because rRNA is relatively well conserved between related species. Moreover, the limited number of sequence variations are often concentrated in the highly structured regions of the rRNA. Therefore, some of the most useful regions of diverse nucleobase sequence suitable for designing organism specific probes are often unavailable to nucleic acid probes.

Because of its unique structure, PNA probes can be designed to target regions of rRNA under conditions of low ionic strength wherein the secondary structure is destabilized. Because PNA probe can efficiently, and preferably, hybridize to nucleic acid under these conditions of low salt, the PNA probes can be designed to target rRNA which cannot be targeted by traditional nucleic acid probes (See: Stefano et al., Diagnostic Applications of PNA Oligomers, Diagnostic Gene Detection and Quantification Technologies for Infectious Agents and Human Genetic Diseases, # 948, IBC Library Series, 19–37 (1997)). Thus, the PNA probes of this invention typically generate stronger signals than can be achieved with nucleic acid probes of comparable nucleobase sequence. Consequently, the PNA probes of this invention do not suffer from the limitations characteristic of nucleic acid probes.

b. PNA Probe Sets

In another embodiment, this invention is directed to a PNA probe set suitable for detecting, identifying or quantitating bacteria and/or eucarya in a sample. The general and preferred characteristics of PNA probes suitable for the detection, identification or quantitation of bacteria and/or eucarya have been previously described herein. Preferred probing nucleobase sequences are listed in Table 1. The grouping of PNA probes within sets characterized for specific detection, identification and/or quantitation of either bacteria or eucarya is contemplated as a preferred embodiment of this invention. The grouping of PNA probes within sets characterized for specific identification and enumeration of both bacteria and eucarya is contemplated as still another preferred embodiment of this invention.

Probe sets of this invention shall comprise at least one PNA probe but need not comprise only PNA probes. For example, probe sets of this invention may comprise mixtures of PNA probes and nucleic acid probes, provided however that a set comprises at least one PNA probe as described herein. In preferred embodiments, some of the probes of the set are blocking probes composed of PNA or nucleic acid.

Table 1 lists four probing nucleobase sequences suitable for the universal detection of bacteria and three probing nucleobase sequences suitable for the universal detection of eucarya. Since alternative probing nucleobase sequences exist for the detection of either bacteria or eucarya, it is preferable to use a probe set containing two or more PNA probes for the detection of either bacteria or eucarya to thereby increase the detectable signal in the assay (For Example: compare Panel I of FIG. 1 with Panels II through V).

One exemplary probe set might therefore comprise probes suitable for the detection of both bacteria and eucarya. Consequently, a suitable probe set might contain at least one PNA probe suitable for detecting bacteria and having a probing nucleobase sequence wherein at least a portion of the probing nucleobase sequence is at least ninety percent homologous to the nucleobase sequence, or their complements, selected from the group consisting of: CTG-CCT-CCC-GTA-GGA; TAC-CAG-GGT-ATC-TAA-T; CAC-GAG-CTG-ACG-ACA and CCG-ACA-AGG-AAT-TTC; and at least one other PNA probe suitable for detecting eucarya and having a probing nucleobase sequence wherein at least a portion of the probing nucleobase sequence is at least ninety percent homologous to the nucleobase sequence, or their complements, selected from the group consisting of: ACC-AGA-CTT-GCC-CTC-C; GGG-CAT-CAC-AGA-CCT-G; TAG-AAA-GGG-CAG-GGA and TAC-AAA-GGG-CAG-GGA.

In a preferred embodiment, probes for detecting bacteria would be independently detectable from probes for detecting eucarya thereby enabling the independent or multiplex detection, identification and/or quantitation of bacteria and eucarya in the same sample and in the same assay. In other embodiments, the probes are not independently detectable yet the bacteria and eucarya are distinguishable based upon unique characteristics such as growth rate or morphology (See: Example 13).

A second exemplary probe set might comprise only those probes suitable for the detection of bacteria. Consequently, a suitable probe set might contain PNA probes comprising at least two, but preferably all, of the probing nucleobase sequences wherein at least a portion of the probing nucleobase sequence is at least ninety percent homologous to the nucleobase sequence, or their complements, selected from the group consisting of: CTG-CCT-CCC-GTA-GGA; TAC-CAG-GGT-ATC-TAA-T; CAC-GAG-CTG-ACG-ACA and CCG-ACA-AGG-AAT-TTC.

Still a third exemplary probe set might comprise only those probes suitable for the detection of eucarya. Consequently a suitable probe set might contain PNA probes comprising at least two, but preferably both, of the probing nucleobase sequences wherein at least a portion of the probing nucleobase sequence is at least ninety percent homologous to the nucleobase sequence, or their complements, selected from the group consisting of: ACC-AGA-CTT-GCC-CTC-C; GGG-CAT-CAC-AGA-CCT-G; TAG-AAA-GGG-CAG-GGA and TAC-AAA-GGG-CAG-GGA.

Exemplary Multiplex PNA-FISH Assays

Because the individual PNA probes of this invention can each be labeled with independently detectable moieties, it is possible to design PNA probe sets wherein each probe of the set is independently detectable. The grouping of PNA probes within probe sets characterized for detecting either or both bacteria and eucarya is contemplated as a preferred embodiment of this invention. For example, fluorophores which have sufficiently different excitation and emission spectra are often used as independently detectable moieties. Exemplary independently detectable fluorophores are derivatives of coumarin, fluorescein and rhodamine. Thus, an assay wherein a PNA probe set comprising two or more PNA probes, each labeled with one of an independently detectable moiety, could be used to independently detect, identify or quantitate, the bacteria and eucarya in the same sample and in the same assay. Consequently, the PNA probes, PNA probe sets, methods and kits of this invention are particularly useful for the rapid, sensitive, reliable and versatile multiplex analysis of bacteria and eucarya in a single sample and/or assay. By versatile we mean that the method is generally applicable despite substantial variability in the nucleobase sequences of the probes or probe length used in the assay.

Example 12 of this specification demonstrates the feasibility of multiplex fluorescent in-situ hybridization using independently detectable PNA probes wherein the individual bacteria and eucarya in the sample are detectable and quantifiable. Example 13 of this specification demonstrates the feasibility of multiplex in-situ analysis of bacteria and eucarya based upon differential growth rates of the organisms which results in clearly distinguishable colony morphology. Importantly, both Examples yield information on identity and enumeration of the organisms present in the sample using the same assay.

c. Methods

In another embodiment, this invention is directed to a method suitable for detecting, identifying and/or quantitating bacteria and/or eucarya in a sample. The general and specific characteristics of PNA probes suitable for the detection, identification or quantitation of bacteria and/or eucarya have been previously described herein. Preferred probing nucleobase sequences are listed in Table 1.

The method for detecting, identifying and/or enumerating bacteria and/or eucarya in a sample comprises contacting the sample with one or more PNA probes suitable for hybridization to a target sequence which is specific yet universal to bacteria or eucarya. In preferred embodiments, the probe comprises a probing nucleobase sequence wherein at least a portion of the probing nucleobase sequence is at least ninety percent homologous to the nucleobase sequence, or their complements, selected from the group consisting of: CTG-CCT-CCC-GTA-GGA; TAC-CAG-GGT-ATC-TAA-T; CAC-GAG-CTG-ACG-ACA; CCG-ACA-AGG-AAT-TTC; ACC-AGA-CTT-GCC-CTC-C; GGG-CAT-CAC-AGA-CCT-G; TAG-AAA-GGG-CAG-GGA and TAC-AAA-GGG-CAG-GGA.

According to the method, bacteria and/or eucarya in the sample are then detected, identified and/or quantitated. Detection, identification and/or enumeration of bacteria and/or eucarya is made possible by correlating hybridization, under suitable hybridization conditions or suitable in-situ hybridization conditions, of the probing nucleobase sequence of a PNA probe to the target sequence of the target organism sought to be detected with the presence, absence or number of the bacteria and/or eucarya in the sample. Typically, this correlation is made possible by direct or indirect detection of the probe/target sequence hybrid.

Media Based Analysis of Bacteria and Eucarya

The methods, kits and compositions of this invention are particularly useful for the rapid probe-based detection, identification and/or enumeration of viable bacteria and/or eucarya. For example, it is possible to use enzyme-linked PNA probes in combination with in-situ analysis of colonies of bacteria or eucarya grown directly on the medium on which they were isolated from the sample (i.e. a filtration membrane) to thereby achieve rapid, sensitive and specific analysis in a manner which was not previously possible (See: Example 13).

The rapid probe-based analysis of growing bacteria and/or eucarya requires very high sensitivity in addition to probe specificity because the cell count is limited during the early stages of cell division. Since this probe-based analysis detects nucleic acid (e.g. rRNA) without regard to the metabolic state of the organism, the analysis of growing bacteria is used to distinguish between viable organisms and dead (non-viable) organisms, the presence of which are not typically considered to cause food or beverage spoilage or contamination.

Enzyme-linked probes are preferred for such analysis since the enzymes can rapidly and repetitively turn over a substrate to thereby achieve signal amplification suitable for high sensitivity detection. Preferred, non-limiting, substrates include chemiluminescent compounds, fluorophores and chromophores. PNA probes are the preferred probe type since they hybridize rapidly to nucleic acid and are generally more specific than nucleic acid probes. Furthermore, PNA probes operate under conditions of low ionic strength (favored conditions for hybridizing to structured rRNA) and they form very stable hybrids. In-situ analysis is preferred since viability of colony forming units (CFU) can be absolutely determined and optionally quantitated by scoring the colonies observed. Dead (non-viable) organisms are not scored because they do not grow into a detectable colony.

In preferred embodiments, the bacteria are grown directly on an isolation medium. Integration of the isolation medium with the growth of the bacteria and/or eucarya eliminates the need for a pre- and post-growth transfer and thereby eliminates the opportunity for error associated therewith. Preferably, the isolation medium is a filter or a membrane filter. Preferred filters are microporous membrane filters such as those sold by Millipore Corporation for the filtration of liquids. Pore sizes of the filter are generally chosen so that the organism will not pass though the pores thereby insuring that all the bacteria or eucarya in the sample is collected on the filter.

After the bacteria or eucarya are grown, typically they are fixed. Cell fixation is a term well known in the art of in-situ hybridization and is generally, but not required as part of the in-situ hybridization process.

Using probe-based in-situ analysis of the isolation medium, the number of colony forming units (CFU) of bacteria and/or eucarya which are detected by the organism specific probe, can be counted or scored (manually or by automated methods) after an appropriate incubation (growth) period. If the bacteria and/or eucarya grow rapidly and the enzyme-linked PNA probes are suitable for high sensitivity analysis, typically, the assay can be performed in 1–4 hours. If the bacteria and/or eucarya grow slowly or a less sensitive detection method is used, the assay may require 1–7 days depending on the rate of organism growth or differential growth rate of the organisms of interest in the assay. Because the bacteria and eucarya are preferably grown directly on the isolation medium, the colonies detected are each representative of a colony forming unit (CFU) isolated from the sample. Since the volume of sample filtered to isolate the organisms is known and since only viable organisms grow, the CFU's per unit volume of sample can be directly determined.

Example 13 of this specification demonstrates using this method for the identification and enumeration of bacteria and eucarya in the same sample and in the same assay. With reference to FIG. 8, soy bean peroxidase labeled PNA probes were used to detect grown bacteria and eucarya isolated from a sample by filtration. Because of the differential growth rate, the micro-colonies of eucarya appear as small dots on the filtration membrane whereas the faster growing bacteria produce very large dots (colonies) in the same time period. Thus, multiplex analysis of the sample is possible, even with probes having identical labeled, if the specificity of the probes is considered in relation to other characteristics such as the relative growth rate or colony morphology of organisms sought to be detected, identified or quantitated in the assay.

Exemplary Assay Formats

The probes, probe sets, methods and kits of this invention are suitable for the detection, identification and/or enumeration of bacteria and/or eucarya. In preferred embodiments, in-situ hybridization is used as the assay format for detecting identifying or quantitating target organisms. Most preferably, in-situ hybridization (FISH or PNA-FISH) is the assay format. Exemplary methods for performing PNA-FISH can be found in: Thisted et al. Cell Vision, 3:358–363 (1996) or WIPO Patent Application WO97/18325, herein incorporated by reference. Methods used to experimentally test specific PNA probes in PNA-FISH assays can be found in Example 12 and 13 of this specification.

Organisms which have been treated with the probes, probe sets or probes contained in the kits of this invention can be detected by several exemplary methods. The cells can be fixed on slides and then visualized with a microscope (See: Example 12), film (See: Example 13), camera and film, luminometer or laser scanning device. Alternatively, the cells can be fixed and then analyzed in a flow cytometer (See for example: Lansdorp et al.; WIPO Patent Application; WO97/14026). Automated slide scanners and flow cytometers are particularly useful for rapidly quantitating the number of target organisms present in a sample of interest.

d. Kits

In yet another embodiment, this invention is directed to kits suitable for performing an assay which detects, identifies or quantitates bacteria and/or eucarya in a sample. The general and preferred characteristics of PNA probes suitable for the detection, identification or quantitation of bacteria and/or eucarya have been previously described herein. Preferred probing nucleobase sequences are listed in Table 1. Furthermore, methods suitable for using the PNA probes or PNA probes sets of a kit to detect, identify or quantitate bacteria and/or eucarya in a sample have been previously described herein.

The kits of this invention comprise one or more PNA probes and other reagents or compositions which are selected to perform an assay or otherwise simplify the performance of an assay used to detect, identify or quantitate bacteria and/or eucarya in a sample. In kits which contain sets of PNA probes, wherein each of at least two probes of the set are used to distinguish between and/or enumerate the bacteria or eucarya in a sample in the same assay, the probes of the set are preferably labeled with independently detectable moieties so that individual bacteria or eucarya can be detected, identified and/or enumerated. In a preferred embodiment, PNA probes of a kit which are used to detect each of the bacteria or eucarya are each labeled with independently detectable fluorophores to thereby enable correlation of the presence of signal from a particular fluorophore with the presence of one of either the bacteria or eucarya in the sample.

e. Exemplary Applications For Using The Invention

The PNA probes, probe sets, methods and kits of this invention are particularly useful for the detection, identification and/or quantitation of bacteria and eucarya (e.g. pathogens) in food, beverages, water, pharmaceutical products, personal care products, dairy products or environmental samples. The analysis of preferred beverages include soda, bottled water, fruit juice, beer, wine or liquor products. Suitable PNA probes, probe sets, methods and kits will be particularly useful for the analysis of raw materials, equipment, products or processes used to manufacture or store food, beverages, water, pharmaceutical products, personal care products dairy products or environmental samples.

Additionally, the PNA probes, probe sets, methods and kits of this invention are particularly useful for the detection of bacteria and eucarya (e.g. pathogens) in clinical samples and clinical environments. Suitable PNA probes, probe sets, methods and kits will be particularly useful for the analysis of clinical specimens, equipment, fixtures or products used to treat humans or animals.

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

This invention is now illustrated by the following examples which are not intended to be limiting in any way.

Example 1

Synthesis of bis-(2-methoxyethyl)amidyl-diglycolic Acid

To 500 mmol of diglycolic anhydride stirring in 800 mL of dichloromethane (DCM) was added dropwise, 1.1 mole of bis(2-methoxyethyl)amine (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried ($Na_2SO_4$), filtered and evaporated to yield 73.8 g (296 mmole; 59% yield). A kugelrorh was then used to remove traces of solvent (product was heated to 60° C. at approximately 180 μM Hg).

Example 2

Synthesis of N-[N"-Fmoc-(2"-aminoethyl)]-N-[N, N'-(2-methoxyethyl)amidyl-diglycolyl]glycine ("Fmoc-"E"aeg-OH")

To 60 mmol of Fmoc-aeg-OH (PerSeptive Biosystems, Inc.) was added 360 mL of MilliQ water, 180 mL of acetone, 120 mmol of $NaHCO_3$ and 60 mmol of $K_2CO_3$. This solution was allowed to stir until all the Fmoc-aeg-OH had dissolved (approx. 2 hr.) and then the solution prepared, as described below, was added.

To 70 mmol of bis-(2-methoxyethyl)amidyl-diglycolic acid was added 120 mL of anhydrous acetonitrile (Fluka Chemical), 240 mmol of N-methylmorpholine (NMM; Fluka Chemical) and 75 mmol of trimethylacetyl chloride (Aldrich Chemical). The solution was allowed to stir at room temperature for 30 minutes and then added dropwise to the solution of Fmoc-aeg-OH which was prepared as described above.

After the combined solutions stirred for 1 hr and tlc analysis indicated complete reaction, 6N HCl was added to the reaction until the pH was less than 2 by paper. The organic solvent was then removed by vacuum evaporation. The remaining aqueous solution was then transferred to a separatory funnel and extracted 2× with 250 mL of ethyl acetate. The combined ethyl acetate layers were dried ($Na_2SO_4$), filtered and evaporated to yield 41.5 g of an oil.

This crude product was purified by column chromatography using a reversed phase stationary phase (C18) and a gradient of aqueous acetonitrile to elute the product and remove the pivalic acid. Though not visible by tlc, the elution of the pivalic acid can be monitored by smell. The pivalic acid can be almost completely eluted from the column prior to elution of the product. Elution of the product can be monitored by tlc. Yield 26.8 g (47 mmol; 78%). This "Fmoc-"E"aeg-OH" monomer was used directly on the PNA synthesis instrument, using standard condensation conditions, or used to prepare prederivatized synthesis supports which were used for the preparation of C-terminally "E" modified PNAs. An "E" modification (subunit) of a PNA or polyamide has the formula:

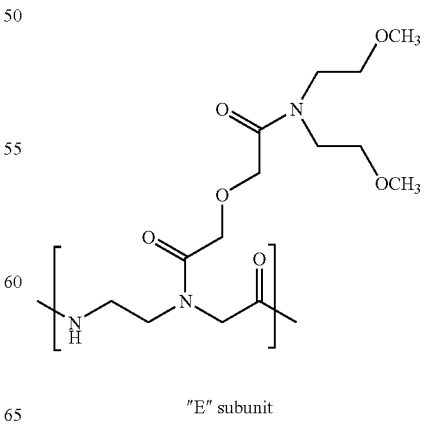

"E" subunit

Example 3

Synthesis of 4-(N-(tert-butyloxycarbonyl)-aminobenzoic Acid

To 100 mM of methyl-4-amino benzoic acid stirring in 150 mL of dioxane was added 110 mM of di-tert-butyl-dicarbonate. The reaction was warmed to 70–80° C. and let stir for about 48 hours. The solvent was then evaporated under reduced pressure and the residue redissolved in about 300 mL of ethylacetate. The organic layer was then washed three times with 10% aqueous citric acid, dried ($Na_2SO_4$), filtered and evaporated to a solid. The solid was then suspended in 150 mL of 1N NaOH and 50 mL acetone. Saponification of the ester was allowed to run overnight until complete hydrolysis was observed by thin layer chromatography (TLC). To the solution was added citric acid until the pH of the solution was approximately 4. The solid was then collected by vacuum filtration and dried in a vacuum oven at 50° C. Yield 20.3 g, 85%. The product was a single peak when analyzed by reversed phase High Performance Liquid Chromatography (HPLC) using 0.1% aqueous trifluoroacetic acid (TFA) and a linear acetonitrile gradient.

Example 4

Synthesis of N-α-(Fmoc)-N-ε-[4-(N-(tert-butyloxycarbonyl)-aminobenzamidyl)]-L-Lysine-OH ("Fmoc-K(P)—OH")

To 2.6 mmol of N-α-(Fmoc)-N-ε-($NH_2$)-L-Lysine-OH was added 5 mL of N,N'-dimethylformamide (DMF) and 2.7 mmol of trifluoroacetic acid. This solution was allowed to stir until the amino acid had completely dissolved.

To 2.6 mmol of 4-(N-(tert-butyloxycarbonyl)-aminobenzoic acid was added 50 mL of DMF, 2.7 mmole of [O-(7-azabenzotriaol-1-yl)-1,1,3,3-tetramethyluronium hexafluorophosphate (HATU), and 15 mmol of diisopropylethylamine (DIEA). To this stirring solution was added, dropwise, the N-α-(Fmoc)-N-ε-($NH_2$)-L-Lysine-OH solution prepared as described above. The reaction was allowed to stir for 30 minutes and was then worked up.

The solvent was vacuum evaporated and the residue partitioned in 100 mL of DCM and 50 mL of 10% aqueous citric acid. The layers were separated and the organic layer washed with aqueous 5% sodium bicarbonate. The product crystallized in the separatory funnel and was collected by vacuum filtration. The solid as stirred in a solution of 30 mL 10% aqueous citric acid and 70 mL DCM and then recollected by vacuum filtration. Yield 1.58 mmol, 60%.

Example 5

Synthesis of PNAs

Unless otherwise stated, PNAs were synthesized using commercially available reagents and instrumentation obtained from PE Biosystems, Foster City, Calif., USA. PNAs having modifications of "E" or "K(P)" ("P" is aminobenzoic acid) were prepared using prederivatized synthesis support or by performing the synthesis using monomers prepared as described above.

Example 6

Synthesis of Arylamine Labeled Peptide Nucleic Acids a. N-Terminal Labeling

Labeling of the amino terminus of the PNA oligomer with a linker group while the oligomer was still support bound was accomplished by condensation of two subunits of Expedite PNA Linker (P/N GEN063032) using one of the auxiliary positions of the PNA synthesizer and the standard coupling cycle. To the amino terminus of the elongated polymer was condensed 4-(N-(tert-butyloxycarbonyl)-aminobenzoic acid (See: Example 3). Condensation of 4-(N-(tert-butyloxycarbonyl)-aminobenzoic acid with the N-terminus was typically performed manually using conditions similar to those used on the PNA synthesizer except that the concentration of reagents and reaction time was usually increased. After desired modification of the amino terminus of the polymer, the oligomers were then cleaved from the support, deprotected and purified using reversed phase HPLC.

b. C-Terminal Labeling

Bulk synthesis support having a prederviatized N-ε-arylamine-L-lysine residue was prepared by condensing N-α-(Fmoc)-N-ε-[4-(N-(tert-butyloxycarbonyl)-aminobenzamidyl)]-L-Lysine-OH ("Fmoc-K(P)—OH") with the PNA synthesis support prior to assembly of the PNA. Condensation of the "Fmoc-K(P)—OH" monomer with the synthesis support was typically performed manually using conditions similar to those used on the PNA synthesizer except that the concentration of reagents and reaction time was typically increased. After desired PNA synthesis and labeling/modification, C-terminal aryl amine modified oligomers were then cleaved from the support, deprotected and purified using reversed phase HPLC.

Example 7

Preferred Method for Removal of the Fmoc Protecting Group

The synthesis support was treated with a solution of 25% piperidine in DMF for 10–15 minutes at room temperature. After treatment, the synthesis support was washed and dried under high vacuum. The support can then be treated with labeling reagent (See: Examples 6 and 8).

Example 8

Preferred Method for Amine Labeling of Support Bound PNA with the NHS Esters of 5(6)carboxyfluorescein (Flu), or 5(and 6)-carboxy-X-rhodamine (Rox)

The amino protecting group (Fmoc) of the assembled PNA was removed and the synthesis support was washed and dried under vacuum. The synthesis support was then treated for 4–5 hours at 30–37° C. with approximately 250 μL of a solution containing 0.08 M NHS ester labeling reagent, 0.24 M DIEA and 0.24 M 2,6-lutidine. After treatment the synthesis support was washed and dried under high vacuum. The PNA oligomer was then cleaved, deprotected and purified using reversed phase HPLC using methods known in the art.

Example 9

General Procedure for Cleavage, Deprotection and Purification

The synthesis support (Fmoc-PAL-PEG/PS; P/N GEN913384) was then removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) was then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods known in the art.

Note: Several PNAs were prepared using new product Fmoc-XAL-PEG/PS synthesis support (P/N GEN 913394) available from PE Biosystems, Foster City, Calif., USA. This support has the advantage that the PNA can be removed more rapidly and under more mildly acid conditions. For PNAs prepared with Fmoc-XAL-PEG/PS the support is treated as described above except that a solution of TFA/m-cresol 9/1 was used for a period of 10–15 minutes (2×).

Example 10

Exemplary Procedures for Preparing Peptide Nucleic Acids (PNAs) Conjugated to Soybean Peroxidase Stock Solutions 1. Probe Stock Purified arylamine terminated probe, typically fifteen or sixteen residues in length, was dissolved at a concentration of approximately 0.33 μmol per milliliter in 50% aqueous N,N'-dimethylformamide (DMF).

2. Enzyme Stock

Soy bean peroxidase, conjugate grade, obtained from Wiley Organics, was dissolved at a concentration of 8.0 mg per milliliter in an aqueous buffer comprised of 0.3 M NaCl, 10 mM $MgCl_2$, 0.1 mM $ZnCl_2$ and 30 mM N-methylmorpholine adjusted to pH 7.6 with 12 N hydrochloric acid.

3. 30% Aqueous DMF

An aqueous DMF solution was prepared by combining three volumes of DMF with 7 volumes of water.

4. MES Buffer

An 0.2 M solution of 4-morpholineethanesulfonic acid (MES) in water was prepared (not pH adjusted).

5. Glycine Solution

A solution comprised of 0.5 M glycine and 0.25 M sodium hydroxide in water was prepared.

6. Wash Buffer

An aqueous buffer comprised of 0.15 M NaCl, 5 mM $MgCl_2$, 0.05 mM $ZnCl_2$ and 15 mM N-methylmorpholine adjusted to pH 7.6 with hydrochloric acid was prepared.

7. Storage Buffer

An aqueous buffer comprised of 0.3 M NaCl, 10 mM $MgCl_2$, 0.1 mM $ZnCl_2$ and 30 mM N-methylmorpholine adjusted to pH 7.6 with 12 N hydrochloric acid was prepared.

8. Stabilization Buffer

Peroxidase Stabilizing Buffer, DAKO Diagnostics Canada Inc.; Part No. D210084

Exemplary Small Scale Conjugation Procedure

Note: This procedure has been successfully scaled at least 10 fold.

In a reaction tube was combined 20 μL of Enzyme Stock, 12.5 μL of 30% Aqueous DMF, and 7 μL of Probe Stock. In a separate tube was placed 1 mg of 1-(3-dimethylaminopropyl)-3-ethylcarbodiimide hydrochloride (EDC) and 10 μL of MES Buffer. These reagents were mixed, just prior to addition to the reaction, until the EDC had dissolved in the MES Buffer. The EDC/MES Buffer solution was then added to the tube containing the enzyme and probe (Reaction Mixture). The contents were mixed, and the tube was placed at 0° C. for 40 min. To the Reaction Mixture was then added 7 μL of Glycine Solution. The contents were again mixed and the tube was placed at 0° C. for a further 20 minutes.

Exemplary Conjugate Purification Procedures

We have used both ultrafiltration and gel filtration chromatography for the purification of the enzyme-linked probe from excess enzyme and excess probe. At this time we prefer to use gel filtration chromatography though these as well as other methods of separation may work equally well. Exemplary methods for both purification procedures will be described below.

Ultrafiltration

As an example of ultrafiltration, the contents of the tube (See: Exemplary Small Scale Conjugation Procedure) were diluted with 50 μL of Wash Buffer and then transferred to the cup of an ultrafiltration device (e.g. 30,000 molecular weight cut-off, Millipore Corporation, Bedford Mass.) and spun at 5,000×g until ~90% of the liquid had been removed from the cup. An additional 50 μL of Wash Buffer was then be added to the cup and the device spun again to remove 90% of the liquid. This washing procedure was preferably repeated two additional times. The contents of the cup were then diluted to a volume of 1 milliliter in Storage Buffer. The absorbance of this solution (at 260 nm) was then used to estimate the concentration of the enzyme conjugate (0.05 absorbance units at 260 nanometers per milliliter is typically estimated to be 0.33 nmol per milliliter based on an estimated extinction for a PNA 15-mer of 150 optical density units per μmole of probe).

Gel Filtration Chromatography

At this time however, we prefer to separate the crude reaction mixture using gel filtration chromoatography (e.g. Superdex 200 (Part No. 17-1043-01) from Amersham Pharmacia or a BioRad prepacked gel filtration BioSelect SEC 250-5 column (Part No. 125-0476)). The mobile phase was aqueous 0.1M NaCl and 0.1M bis-tris HCl (Research Organics; Part No. 1164B) pH 6.5 with 10% acetonitrile. After Gel Filtration Chromatography, the fractions were desalted and resuspended in Stabilization Buffer (this buffer is superior to the Storage Buffer for long term storage of the conjugate). Desalting was performed by loading the fractions on a preconditioned (See: Manufacturers instructions) Oasis™ prepackaged column (Waters; Part No. 094225 (30 mg); 094226 (60 mg) or 106202 (200 mg)). Once loaded, the enzyme conjugate was eluted from the stationary phase using a solution containing 0.01 M NaCl, 0.02 M Tris pH 7.4 with a stepwise (10% per step) gradient of aqueous acetonitrile (usually requiring 30% aqueous acetonitrile to elute the product). The absorbance of this solution (at 260 nm) was then used to estimate the concentration of the enzyme conjugate (0.05 absorbance units at 260 nanometers per milliliter is typically estimated to be 0.33 nmol per milliliter based on an estimated extinction for a PNA 15-mer of 150 optical density units per µmole of probe). The aqueous acetonitrile was removed by vacuum evaporation and the conjugate resuspended in Stabilization Buffer based on the pre-evaporation quantity of conjugate in the sample. Generally, the conjugate was resuspended to a concentration of 10 µM in Stabilization Buffer and stored at −20° C. The SBP labeled probes can optionally be diluted to 100 nM in Stabilization Buffer and stored at 4° C.

Final Probe Preparation

Regardless of which purification method is used, the products are typically screened using dot blot analysis on nylon membrane (See Example 10) to determine sensitivity, specificity and noise. Analysis was performed after the fractions were transferred to Storage Buffer or Stabilization Buffer.

PNA Oligomers Prepared

TABLE 2

| Probe No | Probe ID | Target Organism | PNA Probe Sequence |
|---|---|---|---|
| 1 | Flu-BacUni-1 | Bacteria | Flu-OO-CTG-CCT-CCC-GTA-GGA-NH$_2$ |
| 2 | Flu-BacUni-2 | Bacteria | Flu-OO-TAC-CAG-GGT-ATC-TAA-T-NH$_2$ |
| 3 | Flu-BacUni-3 | Bacteria | Flu-OO-CAC-GAG-CTG-ACG-ACA-NH$_2$ |
| 4 | Flu-BacUni-4 | Bacteria | Flu-OO-CCG-ACA-AGG-AAT-TTC-NH$_2$ |
| 5 | SBP-BacUni-1 | Bacteria | SBP-P-OO-CTG-CCT-CCC-GTA-GGA-NH$_2$ |
| 6 | SBP-BacUni-2 | Bacteria | SBP-P-OO-TAC-CAG-GGT-ATC-TAA-T-NH$_2$ |
| 7 | SBP-BacUni-3 | Bacteria | SBP-P-OO-CAC-GAG-CTG-ACG-ACA-NH$_2$ |
| 8 | SBP-BacUni-4 | Bacteria | SBP-P-OO-CCG-ACA-AGG-AAT-TTC-NH$_2$ |
| 9 | SBP/Flu-BacUni-1 | Bacteria | Flu-OEE-CTG-CCT-CCC-GTA-GGA-EOO-K(P-SBP)-NH$_2$ |
| 10 | Flu-EuUni-1 | Eucarya | Flu-OO-ACC-AGA-CTT-GCC-CTC-C-NH$_2$ |
| 11 | Flu-EuUni-2 | Eucarya | Flu-OO-GGG-CAT-CAC-AGA-CCT-G-NH$_2$ |
| 12 | Flu-EuUni-3 | Eucarya | Flu-OOE-TAG-AAA-GGG-CAG-GGA-EE-NH$_2$ |
| 13 | Flu-EuUni-4 | Eucarya | Flu-OEE-TAC-AAA-GGG-CAG-CCA-EE-NH$_2$ |
| 14 | SBP-EuUni-1 | Eucarya | SBP-P-OO-ACC-AGA-CTT-GCC-CTC-C-NH$_2$ |
| 15 | SBP-EuUni-2 | Eucarya | SBP-P-OO-GGG-CAT-CAC-AGA-CCT-G-NH$_2$ |
| 16 | Flu-BacUni-1EE | Bacteria | Flu-OO-CTG-CCT-CCC-GTA-GGA-EE-NH$_2$ |
| 17 | Rox-EuUni-1EE-15mer | Eucarya | Rox-OO-CCA-GAC-TTG-CCC-TCC-EE-NH$_2$ |

All PNA sequences are written from the amine (N—) terminus to the carboxyl (C—) terminus. Flu 5(6)-carboxyfluorescein, Rox=5(and 6)-carboxy-X-rhodamine; SBP=soy bean peroxidase; P=4-aminobenzoic acid; K=L-lysine; E is defined above; and O=8-amino-3,6-dioxaoctanoic acid.

Example 11

General Methods for Dot Blot Analysis

RNA Preparation

Using a Qiagen kit (P/N 75144), total RNA (including app. 80% rRNA) was isolated from the different bacteria or eucarya cells which had been grown in culture. The total concentration of isolated RNA was determined by measuring the absorption at 260 nm.

PNA Probe Hybridization to the Membranes

Note: The text which has been bracketed and underlined was a modification to the procedure which was used to generate the results presented in FIGS. 4, 5 and 7 (optimized for SBP labeled PNA probes). This is the preferred procedure as can be seen by the improved signal to noise ratio when compared with the images presented in FIG. 2.

Dot blots were made on nylon membranes obtained from Gibco-BRL (P/N 14830-012). For the rRNA of each cultured bacteria or eucarya, a dilution row containing at least 5 spots was made, starting with a concentration of approximately 16 µg/µL RNA for the strongest solution and continuing with half log dilutions in diethyl pyrocarbonate (DEPC) treated water (RNase free). Prior to spotting on the membrane, each dilution stock was heated to 68° C. for three minutes. The spotting produced a half log dilution series containing approximately 16, 5.1, 1.6, 0.52, 0.17 ng . . . (etc.) total RNA per spot. Once the spots had air dried, the membrane was UV-crosslinked and then stored in a plastic bag until used.

When used, individual membranes were placed in plastic bags and pre-wet with RNase free water. The membranes were prehybridized in Hybridization Buffer (20 mM Tris-HCl, pH 7.5; 50% formamide; 0.1% sodium dodecyl sulfate (SDS); and 100 mM NaCl) for 15 minutes at 50° C. [The membranes were prehybridized in Hybridization Buffer 2 (20 mM Tris-HCl, pH 9.5; 50% formamide; 1× Denhardt's Solution (USB, P/N US70468); 0.7% polyoxyethylene-sorbitan monolaurate (Tween 20, Sigma P/N P-1379); and 100 mM NaCl) for 15 minutes at 50° C. All fluorescein labeled probes were diluted in 1:1 DMF/H$_2$O to a concentration of approximately 300 pmole/µL and then diluted to a final concentration of 5 pmol/mL each using Hybridization Buffer. All SBP labeled probes were prepared and diluted as described in Example 10. The prehybridization buffer was removed from the bags and fresh hybridization buffer containing the PNA probe(s) of interest was(were) added to the bags. The appropriate probe(s) was(were) typically used at a final concentration of 5 pmol/mL each for Fluorescein labeled PNAs or 1 pmol/mL for SBP labeled PNAs (except for Panels I and II of FIG. 4, wherein 5 pmol/mL of the bis labeled probe (SBP/Flu-BacUni-1) was used for direct comparison).

Probe hybridization was performed at 50° C. for 1 hour except that SBP probes were hybridized for 30 minutes. The filters treated with Fluorescein labeled probes were then washed 3 times in TE-7.5 (10 mM Tris-HCl, pH 7.5, 1 mM EDTA) containing 0.2% SDS at ambient or elevated temperature. The filters treated with SBP labeled probes were then washed 3 times in TE-9.0 (10 mM Tris-HCl, pH 9.0, 1 mM EDTA) containing 0.2% Tween 20 at elevated temperature. [The wash buffer was also modified whereby the 10 mM Tris was replaced with 10 mM Capso (Sigma P/N C-1254) pH 10.]

RNA Spotted Membranes

With reference to FIG. 1 (Panels I, II, III, IV and V), the total-RNA of each of the following bacteria were spotted on membranes in the columns illustrated: A *Pseudomonas aeruginosa*, B *Escherichia coli*, C *Staphylococcus aureus* and D *Salmonella typhimurium*.

Figure 2:
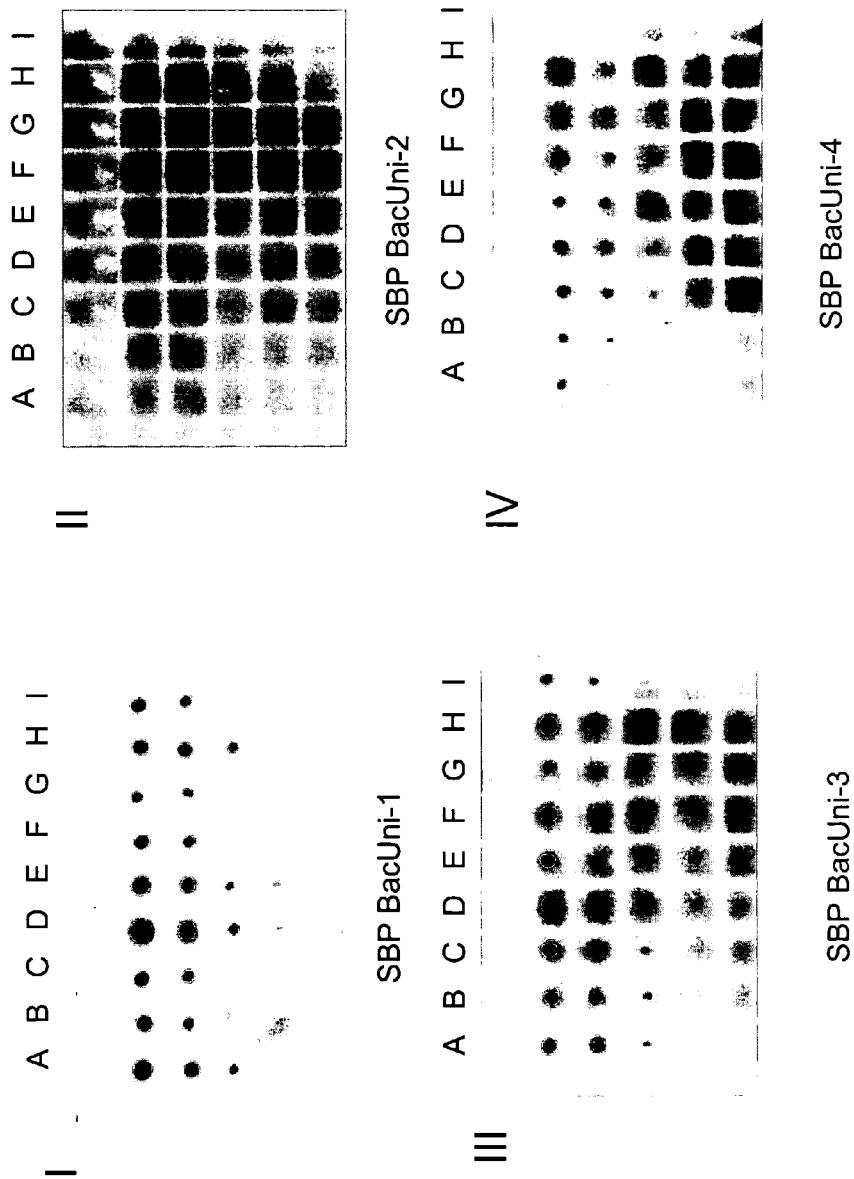
FIGS. 2-I through 2-IV are electronic images of dot blot assays used to examine the universal detectability of 4 different soy bean peroxidase labeled PNA oligomers directed to target sequences in the rRNA of bacteria.
Figure 4:
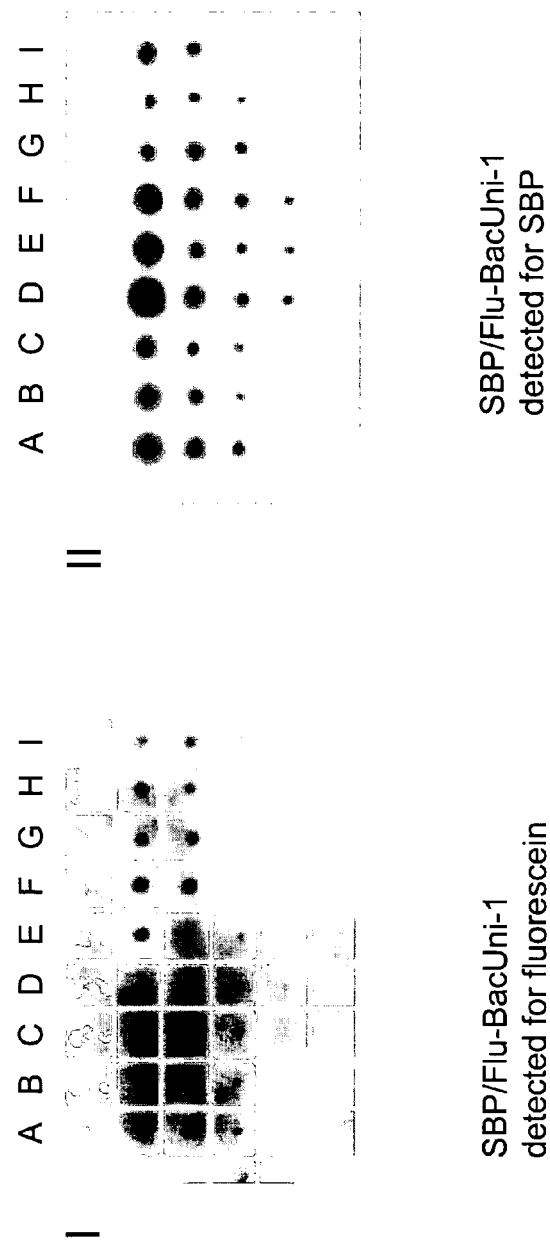
FIGS. 4-I and 4-II are electronic images of dot blot assays used to compare the detection limits of a universal bacterial PNA probe labeled with both an enzyme (soy bean peroxidase) and a hapten (fluorescein).

With reference to FIG. 2 (Panels I, II, II and IV) and FIG. 4 (Panels I and II), the total-RNA of each of the following bacteria were spotted on membranes in the columns illustrated: A *Pseudomonas fluorescens*, B *Pseudomonas aeruginosa*, C *Pseudomonas cepatia*, D *Pseudomonas putida*, E *Escherichia coli*, F *Bacillus subtilis*, G *Staphylococcus epidermidis*, H *Staphylococcus aureus*, and I *Salmonella typhimurium*.

Figure 3:
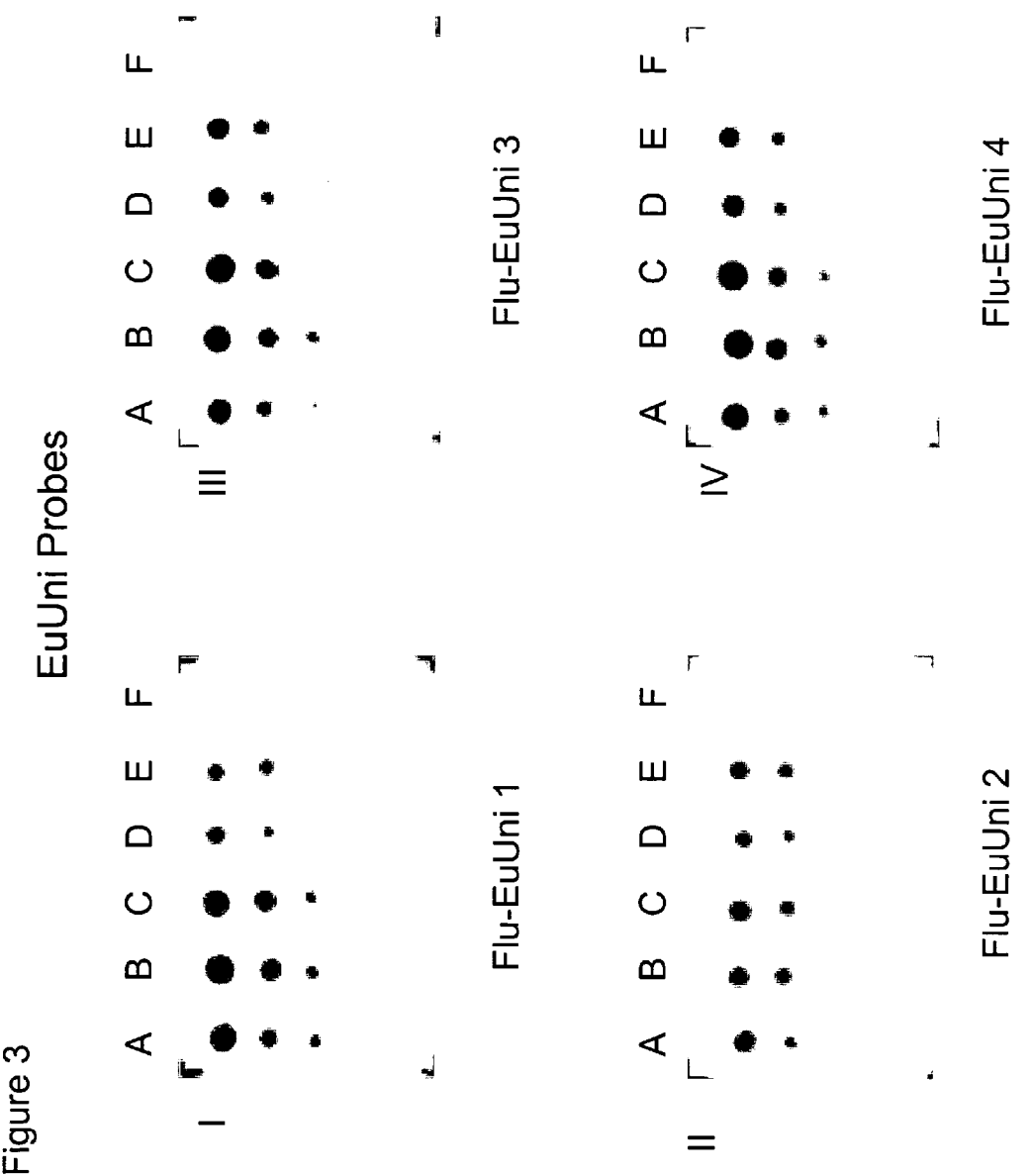
FIGS. 3-I through 3-IV are electronic images of dot blot assays used to examine the universal detectability of 4 different fluorescein labeled (fluorescein used as a hapten in the experiment) PNA oligomers directed to target sequences in the rRNA of eucarya.

With reference to FIG. 3 (Panels I, II, III and IV), the total-RNA of each of the following organisms or tissues were spotted on membranes in the columns illustrated: A Human spleen, B Mouse spleen, C Rat Kidney, D *Saccaharomyces cerevisiae*, E *Dekerra brettanomyces* and F *E. coli*.

Figure 5:
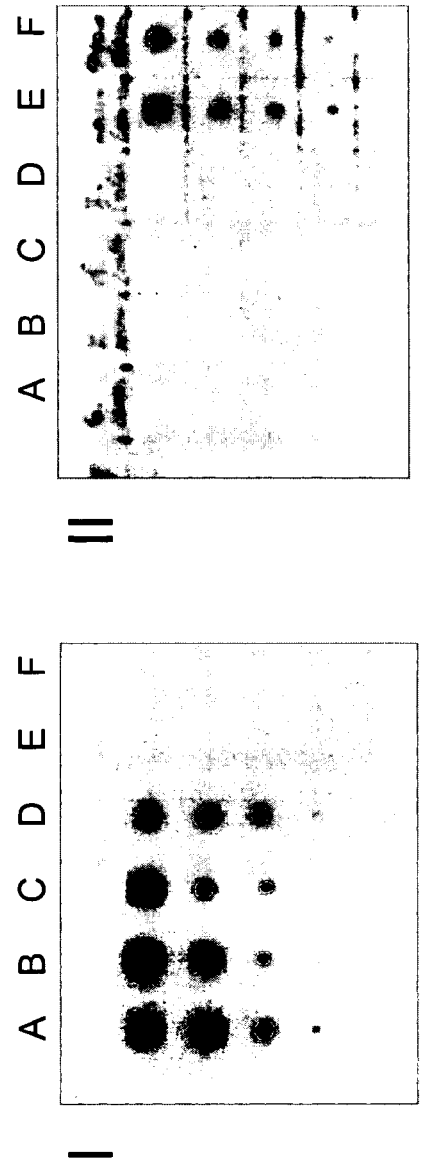
FIGS. 5-I and 5-II are electronic images of dot blot assays used to compare the specificity of PNA probes for either eucarya (Panel I) or bacteria (Panel II).
Figure 7:
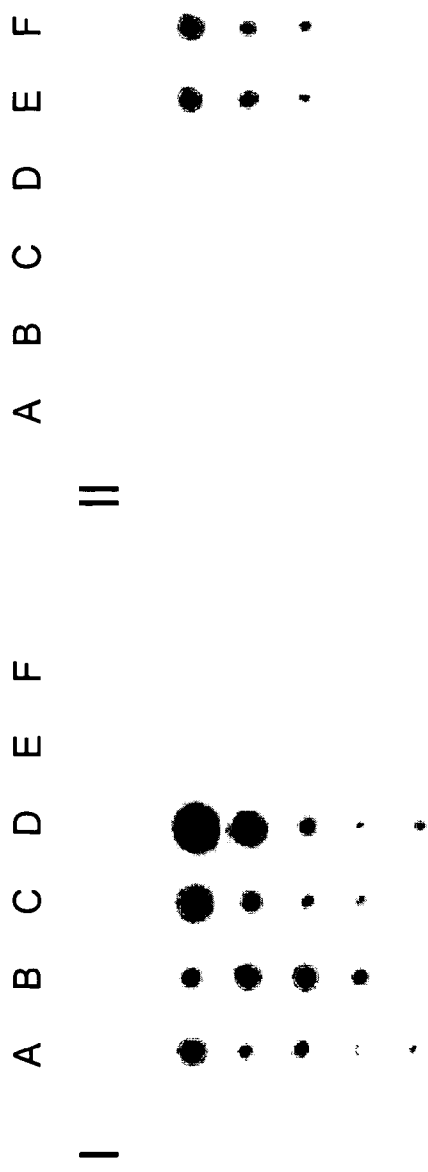
FIGS. 7-I and 7-II are electronic images of dot blot assays used to compare the specificity of PNA probe mixtures for either eucarya (Panel I) or bacteria (Panel II).

With reference to FIG. 5 (Panels I and II) and FIG. 7 (Panels I and II), the total RNA of each of the following organisms were spotted on membranes in the columns illustrated: A *S. cerevisiae*, B *Zygosaccaharomyces rouxii*, C *Dekerra intermedia*, D *Zygosaccaharomyces balii*, E *Lactobacillus brevis* and F *Pediococcus damnosus*.

Visualization of the Membrane

1. For Fluorescein Labeled Probes

After the washes were completed, the membranes were treated with a blocking solution (50 mM Tris-HCl, pH 9.0; 0.5 M NaCl; and 0.5% casein). The starting temperature of the solution was 65° C., but the solution cooled as the blocking proceeded with shaking at room temperature for 15 minutes. An anti-fluorescein-alkaline phosphatase conjugate (Rabbit (Fab) anti-FITC/AP (DAKO A/S, P/N K0046)) was diluted 1:1000 in blocking solution and the membranes were left shaking in this solution for 30 minutes at room temperature. The membranes were then washed in a washing solution (50 mM Tris-HCl, pH 9.0; 0.5 M NaCl; and 0.5% Tween-20) three times each for 5 minutes. To prepare the membranes for the detection, a final rinse was performed (10 mM Tris-HCl, pH 9.5; 10 mM NaCl; and 1 mM $MgCl_2$). The chemiluminescent substrate (AMPPD, Tropix Corp., P/N PD025) was diluted 1:100 in an aqueous Substrate Solution (0.1 M diethanolamine, pH 9.7; and 1 mM $MgCl_2$) and the membranes were immersed without shaking for 4 minutes. The membranes were placed in a plastic bag and excess substrate was squeezed out and the bag sealed. The membranes were exposed to Fuji-RX X-ray film for between 5 and 30 minutes.

Note: The membranes used to generate FIG. 3 were treated as Follows: Hybridization Buffer 2 was used as the modified wash buffer. In addition, CDP* (Tropix P/N MS025) was used as the substrate diluted 1:1000 in Substrate Solution.

2. For SBP Labeled Probes

After the washes were completed, the chemiluminescent substrate (Pierce 17015) was mixed 1:1 and $CaCl_2$ added to a final concentration of 50 mM. The membranes were immersed in the substrate without shaking for 2 minutes. The membranes were placed in a plastic bag and excess substrate was squeezed out and the bag sealed. The membranes were exposed to Fuji-RX X-ray film for between 1 and 15 minutes.

Results

With reference to FIG. 1, Panels I through V, the spotted RNA of four species of bacteria was easily detected using each of the individual the fluorescein labeled PNA probes (Probe Nos. 1, 2, 3 and 4) directed to bacteria (Panels II through V) and a mixture of all four fluorescein labeled PNA probes (Probe Nos. 1, 2, 3, and 4; Panel I) directed to bacteria. The limit of detection was visibly improved by approximately 1 log unit when using the PNA probe mixture (Panel I). This data demonstrated the universal nature of the fluorescein labeled PNA probes for the detection of bacteria and the improvement in the limit of detectability when using a mixture of several universal PNA probes.

With reference to FIG. 2, Panels I through IV, the spotted RNA of eight species of bacteria was easily detected using each of the SBP labeled PNA probes (Probe Nos. 5, 6, 7 and 8). This data demonstrated the universal nature of the SBP labeled PNA probes for the detection of bacteria. When taken as a whole, the data presented in FIGS. 1 and 2 demonstrates that both PNA probes labeled with either detectable moiety (SBP v. fluorescein) are suitable for universal detection of target nucleic acid sequences of bacteria.

With reference to FIG. 3, Panels I, II, III and IV the spotted RNA of five species of multicellular and single cellular organisms was easily detected using each of the individual the fluorescein labeled PNA probes (Probe Nos., 10, 11, 12 and 13). Probes 12 and 13 did yield a slightly detectable cross reaction to the bacterial species (*E. coli*) but this was very mild as compared with the specific signal detected in the presence of the rRNA of the yeasts. Moreover, more stringent washing would likely result in elimination of the non-specific signal. Curiously, the perfectly complementary probe no. 13, exhibited less cross reaction as compared with the less homologous probe no. 12. Nevertheless, this data demonstrated the universal nature of the fluorescein labeled PNA probes for the detection of eucarya. Similar results have been obtained with SBP labeled PNA probes based on EuUni-1 and EuUni-2. These results taken as a whole demonstrate that PNA probes labeled with either detectable moiety (SBP v. fluorescein) are suitable for universal detection of target nucleic acid sequences of eucarya.

With reference to FIG. 4, Panels I and II, the spotted RNA of all bacteria was easily detected using a PNA probe labeled with both fluorescein and SBP (bis labeled PNA probe; Probe No. 9). This data demonstrated the universal nature of the bis-labeled PNA probe for the detection of the eight species of bacteria, as well as providing a means to directly compare SBP and fluorescein labeled PNA probes. The data indicates that while both labels are detectable, detection of the SBP label provides greater sensitivity and better signal to noise ratios under the conditions examined.

With reference to FIG. 5 (Panels I and II), the spotted RNA of either eucarya or bacteria was detected with the appropriate PNA probe (for eucarya (Panel I), Probe No. 14/SBP-EuUni-1 was used; and for bacteria (Panel II); Probe No. 5/SBP-BacUni-1 was used). The data demonstrated that both probes exhibited very good specificity for intended target organism while no significant cross reaction was observed with the RNA of the non-target organisms.

With reference to FIG. 7 (Panels I and II), the spotted RNA of either eucarya or bacteria was detected with the mixtures of the appropriate PNA probe (for eucarya (Panel I), PNA probes Probe Nos. 14 and 15 were used; and for bacteria (Panel II); PNA probes Seq. ID Nos. 5, 6, 7 and 8 were used). The data demonstrated that both probes exhibited very good specificity for intended target organism while no significant cross reaction was observed with the RNA of the non-target organisms.

Example 12

Multiplex PNA-FISH

A 3 mL culture of *E. coli* was grown overnight in Tryptic Soy Broth (TSB) at 30° C. Absorbance at 600 nm was measured and the culture was diluted into fresh TSB until the absorbance at 600 nm was 0.5 OD/mL. This diluted culture stock was then allowed to double 3–4 times before harvesting. Cells from a 20 mL culture were pelleted by centrifugation at 8000 rpm for 5 minutes, resuspended in 20 mL PBS (7 mM $Na_2HPO_4$; 3 mM $NaH_2PO_4$; 130 mM NaCl), pelleted again and resuspended in Fixation Buffer (3% paraformaldehyde in PBS). The bacteria were incubated at room temperature for 30–60 minutes before they were pelleted again (centrifugation at 8000 rpm for 5 minutes). After removal of the fixation solution, the cells were resuspended in 20 mL of 50% aqueous ethanol. The fixed bacteria may be used after 30 minutes of incubation or stored at −20° C. for up to several weeks before being used.

Similarly, a 3 mL culture of *Saccharomyces cerevisiae* was grown overnight in YM (Difco: DF 0711-17-1) at 25° C. Absorbance at 600 nm was measured and the culture was diluted into fresh YM until the absorbance at 600 nm was 0.5 OD/mL. This diluted culture stock was then allowed to double 3–4 times before harvesting. Cells from a 20 mL culture were fixed as described above.

To 100 µL of each of these two preparations of fixed cells (*E. coli* and *Saccharomyces cerevisiae*) in 50% aqueous ethanol were mixed, centrifuged at 10,000 R.P.M. for 4 min. The aqueous ethanol was then removed from the sample and the pellet was resuspended in 100 µL of sterile PBS and pelleted again by centrifugation at 10,000 R.P.M. for 4 min.

The PBS was then removed from the pellet, and the cells were resuspended in 100 µL of hybridization buffer (20 mM Tris-HCl, pH 9.0; 100 mM NaCl; 0.5% SDS) which contained the appropriate probe (Flu-BacUni-1 EE (Probe No. 15) and Rox-EuUni-1 EE (Probe No. 16)) each at a concentration of 30 pmol/mL. The hybridization was performed at 55° C. for 30 minutes.

The sample was then centrifuged at 10,000 R.P.M. for 4 min. The hybridization buffer was removed and the cells resuspended in 500 µL sterile TE-9.0 (10 mM Tris-HCl, pH 9.0; 1 mM EDTA). The solution was allowed to stand at 55° C. for 10 minutes. The sample was then centrifuged at 10,000 R.P.M. for 10 min. The TE-9.0 was removed from the pellet. This TE-9.0 wash was repeated two more times.

After the final wash, the cells were resuspended in 100 µL TE-9.0. An aliquot of 2 µL of this suspension of cells was placed on a glass slide, spread and allowed to dry. Next, 1–2 µL of Vectashield (Vector Laboratories, P/N H-1000) was deposited over the dried cells and a coverslip was added to the slide and its position fixed using a couple of drops of nail polish.

The bacteria were then observed using a Nikon fluorescent microscope equipped with a 60×immersion oil objective, a 10×ocular (total enlargement is 600 fold) and light filters obtained from Omega Optical (XF22 (green), XF34 (red)) and from Chroma Technology Corp. (Triple filter (DAPI/FITC/TRITC)). Electronic digital images were made of the slide using a SPOT CCD-camera and software obtained from Diagnostic Instruments, Inc., Sterling Heights, Mich. (USA).

The digital images obtained, all covering the same section of the slide, are presented in FIGS. 6-I through 6-IV. In FIG. 6-I (red image), yeast cells are stained red by the Rox-EuUni-1 EE (probe no. 17). In FIG. 6-II (green image), *E. coli* is stained green by the Flu-BacUni-1 EE (probe no. 16). In FIG. 6-II (triple color image) both yeast and bacteria are visualized as a green image as the field has been photographed using the cameras green filter. Clearly the distribution of yeast and bacteria cells are seen as a visual composite of the images presented in FIGS. 6-I and 6-II. In FIG. 6-IV, a digitally created composite of the red and the green images from FIGS. 6-I and 6-II is presented for comparison with the camera images presented in Panels I, II and III. These figures clearly demonstrate that simultaneous detection of a eucarya (represented by *S. cerevisiea*) and a bacteria (represented by *E. coli*) in the same sample (multiplexing) is possible using PNA probes. Though the multiplex analysis described herein is performed manually by visual inspection of the digital images, software is available for performing such a comparison to thereby generate quantitative data for each of the target organisms present in the sample.

Example 13

Rapid Identification and Enumeration of Colonies of Bacteria and Yeast

I. Preparation of Yeast and Bacteria

An overnight culture of *E. coli* was grown to produce the bacteria for this Example. Similarly, an overnight culture of *S. cerevisiae* was grown to produce the yeast for this Example. From the bacteria culture, three sequential 100 fold dilutions were made using 1×PBS as the diluent. From the yeast culture, two sequential 100 fold dilutions were made using PBS as the diluent. To prepare an exemplary sample, 500 µL of each of the final dilutions of the bacteria and the yeast were added to 50 mL of PBS. A 5 mL aliquot of this exemplary sample, containing yeast and bacteria, was then filtered through a 0.45µ PVDF membrane (Millipore; P/N HVLP04700). This filtration was repeated to prepare several membrane filters which could be used to analyze the *E. coli* and *S. cerevisiae* present in the exemplary sample.

II. Membrane-Based In-Situ Hybridization

Membranes were aseptically transferred to a petripad soaked with 2 mL of YM-medium (Sigma P/N L3022) in a small petridish and incubated between 1.5 and 18 hours at 30° C. *E. coli* required as little as 1–2 hours of incubation at 37° C. before detectable micro-colonies were visible (data not shown). However, the slower growing *S. cerevisiae* yeast required an overnight culture (approximately 18 hours) before the micro-colonies were clearly visible using the probes and methods described herein.

Prior to hybridization with PNA probe(s), micro-colonies were fixed to the membrane by placing the membrane on another petripad soaked with 1.5 mL of Fixation Solution (0.5% glutaraldehyde in ethanol with 10% Peroxidase Blocking Reagent; DAKO P/N S2001) for 5 minutes. Probe hybridization was performed for 30 minutes at 50° C. in a petrislide (Millipore; P/N PDMA 04700) with cover using 5 nM each of one or two SBP-labeled PNA probes (Probe No. 5 for detection of bacteria and Probe No. 14 for detection of eucarya) in Hybridization Buffer 3 (25 mM Tris-HCl, pH 9.5), 1× Denhardt's solution, 50% (v/v) formamide, 0.7% (v/v) Tween 20, 1% Casein, 0.1 M NaCl, 5 mM EDTA). Excess probe was removed by washing the filters for four times seven minutes in wash solution (10 mM CAPSO (pH 10.0), 0.2% (v/v) Tween 20). Hybridized probe was then visualized by a two minute chemiluminescent reaction using 500 μL substrate (SuperSignal, Pierce) followed by a 15 minutes exposure on X-ray film (Fuji).

With reference to FIGS. 8I–8III, the three membrane filters (appearing in Panels I, II and III) were all grown for approximately 18 hours and then treated with individual PNA probes or a mixture of Probe No. 5 (for detection of bacteria) and Probe No. 14 (for detection of eucarya). In panel I, only Probe No. 14 was used in the hybridization. The colonies observed were small because the yeast grows slowly. The small spots represent colony forming units of *S. cerevisiae* present in the volume of the exemplary sample which was filtered onto the membrane. In panel III, only Probe No. 5 was used in the hybridization. The colonies observed were very large because the bacteria grow rapidly to form large colonies within 18 hours. Each large spot represents a colony forming unit of *E. coli* present in the volume of the exemplary sample which was filtered onto the membrane. In panel II, a mixture of both Probe No. 5 and Probe No. 14 was used in the hybridization. Consequently, small colonies of *S. cerevisiae* and large colonies of *E. coli* are visible in the Figure wherein the spots represent colony forming units present in the volume of the exemplary sample which was filtered onto the membrane. Taken as a whole, this Example demonstrates the feasibility of multiplex culture analysis of bacteria and eucarya using target specific probes comprising identical labels wherein differentiation is based on culture characteristics (growth rate or morphology) of the organism.

Equivalents

While this invention has been particularly shown and described with references to preferred embodiments thereof, it will be understood by those of ordinary skill in the art that various changes in form and details may be made therein without departing from the spirit and scope of the invention as defined by the appended claims. Those skilled in the art will be able to ascertain, using no more than routine experimentation, many equivalents to the specific embodiments of the invention described herein. Such equivalents are intended to be encompassed in the scope of the claims.

We claim:

1. A method comprising:
a) filtering a sample containing bacteria and yeast through at least one filter;
b) treating the filter or filters with a medium which facilitates the growth of the bacteria and yeast;
c) growing the bacteria and yeast on the filter or filters to thereby produce colonies or microcolonies of the bacteria and yeast;
d) fixing the colonies or microcolonies to the filter or filters;
e) treating each filter under suitable hybridization conditions with one or more enzyme labeled PNA probes wherein, each PNA probe comprises a probing nucleobase sequence complementary to a target sequence in the nucleic acid of the bacteria and/or yeast;
f) removing excess enzyme labeled PNA probe from each of the filters;
g) determineing enzyme activity remaining on each filter to thereby identify or enumerate colonies or microcolonies on the filter or filters.

2. The method of claim 1, wherein identification or enumeration of the colonies or microcolonies depends upon relative growth rate.

3. The method of claim 1, wherein identification or enumeration of the colonies or microcolonies depends upon colony morphology.

4. The method of claim 1, wherein one filter is used to identify or enumerate at least one bacteria and at least one yeast.

5. The method of claim 1, wherein two or more filters are used; at least one filter for each organism to be identified or enumerated.

6. The method of claim 1, wherein two or more enzyme labeled PNA probes are used; at least one PNA probe for each organism to be determined.

7. The method of claim 1, wherein the enzyme labeled PNA probe is a soy bean peroxidase labeled PNA probe.

8. The method of claim 1, wherein the enzyme labeled PNA probe is an orthogonally labeled PNA probe comprising both a fluorophore and enzyme.

* * * * *